US012669510B2

(12) United States Patent
Choung et al.

(10) Patent No.: US 12,669,510 B2
(45) Date of Patent: Jun. 30, 2026

(54) tTG-DGP BIOMARKERS FOR MONITORING CELIAC DISEASE

(71) Applicants: Vibrant Holdings, LLC, Santa Clara, CA (US); Mayo Foundation For Medical Education And Research, Rochester, MN (US)

(72) Inventors: Rok Seon Choung, Rochester, MN (US); Eric V. Marietta, Rochester, MN (US); Vasanth Jayaraman, San Mateo, CA (US); Karthik Krishna, Foster City, CA (US); Joseph A. Murray, Rochester, MN (US)

(73) Assignees: Vibrant Holdings, LLC, Santa Clara, CA (US); Mayo Foundation For Medical Education And Research, Rochester, MN (US)

( * ) Notice: Subject to any disclaimer, the term of this patent is extended or adjusted under 35 U.S.C. 154(b) by 1114 days.

(21) Appl. No.: 17/283,852

(22) PCT Filed: Oct. 8, 2019

(86) PCT No.: PCT/US2019/055249
§ 371 (c)(1),
(2) Date: Apr. 8, 2021

(87) PCT Pub. No.: WO2020/076859
PCT Pub. Date: Apr. 16, 2020

(65) Prior Publication Data
US 2021/0341493 A1 Nov. 4, 2021

Related U.S. Application Data

(60) Provisional application No. 62/742,863, filed on Oct. 8, 2018.

(51) Int. Cl.
| | |
|---|---|
| *G01N 33/68* | (2006.01) |
| *C07K 14/00* | (2006.01) |
| *C07K 16/18* | (2006.01) |
| *G01N 33/543* | (2006.01) |
| *G01N 33/564* | (2006.01) |

(52) U.S. Cl.
CPC ....... *G01N 33/6893* (2013.01); *C07K 14/001* (2013.01); *C07K 16/18* (2013.01); *G01N 33/5432* (2013.01); *G01N 33/564* (2013.01); *G01N 2333/91085* (2013.01); *G01N 2800/24* (2013.01); *G01N 2800/52* (2013.01)

(58) Field of Classification Search
CPC ...................... G01N 2800/24; G01N 33/6893
USPC ........................................................ 435/7.1
See application file for complete search history.

(56) References Cited

U.S. PATENT DOCUMENTS

| | | | |
|---|---|---|---|
| 10,900,964 | B2 | 1/2021 | Rajasekaran et al. |
| 2002/0076834 | A1 | 6/2002 | Detlef et al. |
| 2002/0086319 | A1 | 7/2002 | Ellson et al. |
| 2003/0148401 | A1 | 8/2003 | Agrawal et al. |
| 2003/0228605 | A1 | 12/2003 | Slootstra et al. |
| 2004/0027093 | A1 | 2/2004 | Tashiro et al. |
| 2005/0240811 | A1 | 10/2005 | Safford et al. |
| 2005/0260770 | A1 | 11/2005 | Cohen et al. |
| 2011/0190210 | A1 | 8/2011 | Adini et al. |
| 2011/0293644 | A1 | 12/2011 | Anderson et al. |
| 2012/0172309 | A1 | 7/2012 | Dal Farra et al. |
| 2013/0109034 | A1 | 5/2013 | Kumar et al. |
| 2016/0040703 | A1 | 2/2016 | Schnaufer et al. |
| 2017/0269077 | A1* | 9/2017 | Rajasekaran .......... A61K 39/00 |
| 2018/0106795 | A1 | 4/2018 | Rajasekaran et al. |
| 2021/0285948 | A1 | 9/2021 | Rajasekaran et al. |

FOREIGN PATENT DOCUMENTS

| | | |
|---|---|---|
| CN | 103675291 A | 3/2014 |
| EP | 3864413 A1 | 8/2021 |
| JP | 2008-508856 A | 3/2008 |
| JP | 2015-509583 A | 3/2015 |
| JP | 2017-516118 A | 6/2017 |
| JP | 2017-532544 A | 11/2017 |
| WO | 98/03872 A2 | 1/1998 |
| WO | 2003/104273 A2 | 12/2003 |
| WO | 2007/078868 A1 | 7/2007 |
| WO | 2011/027048 A1 | 3/2011 |
| WO | 2011/038138 A1 | 3/2011 |
| WO | 2013/119845 A1 | 8/2013 |
| WO | 2016/040703 A1 | 3/2016 |

OTHER PUBLICATIONS

Van Der Wal Small intestinal T cells of celiac disease patients recognize a natural pepsin fragment of gliadin, (Proc. Natl. Acad. Sci. USA, 1998, 95:10050-10054.
Robinson Optimizing the stability of single-chain proteins by linker length and composition mutagenesis Proc. Natl. Acad. Sci., 1998, 95:5929-5934.
Dai et al., Evaluation of a recombinant multiepitope peptide for serodiagnosis of Toxoplasma gondii infection, Clinical and Vaccine Immunology, 2012, pp. 338-342).
Da Silveira et al., Chagas disease: recombinant Trypanosoma cruzi antigens for serological diagnosis, Trends in Parasitology, 2001, 17(6):286-291.
Ripalti et al., Construction of Polyepitope fusion antigens of human cytomegalovirus ppUL32: Rectivity with human antibodies, Journal of Clinical Microbiology, 1994, pp. 358-363.

(Continued)

*Primary Examiner* — Gregory S Emch
*Assistant Examiner* — Omar Ramadan
(74) *Attorney, Agent, or Firm* — Goodwin Procter LLP

(57) ABSTRACT

The present disclosure relates generally to biomarkers and peptide arrays, and, more particularly, to a method of using a peptide array to identify biomarkers for an autoimmune disease such as, e.g., Celiac disease. Furthermore, a set of novel biomarkers for Celiac disease, having high sensitivity and specificity, are disclosed in addition to method of treatment using the novel biomarkers.

6 Claims, 11 Drawing Sheets

Specification includes a Sequence Listing.

(56) References Cited

OTHER PUBLICATIONS

Choung, R.S. et al., "Determination of B-Cell Epitopes in Patients with Celiac Disease: Peptide Microarrays," PLOS One, Jan. 29, 2016, e0147777, pp. 1-16, vol. 11, No. 1.

Beyer, M. et al., "Combinatorial Synthesis of Peptide Arrays onto a Microchip," Science, vol. 318, Dec. 21, 2007, p. 1888.

Beyer, M. et al., "Supporting Online Material for Combinatorial Synthesis of Peptide Arrays onto a Microchip," Science, vol. 318, Dec. 21, 2007, 6 pages.

Piehler, J. et al., "Protein Interactions in Covalently Attached Dextran Layers," Colloid and Surfaces B: Biointerfaces 13 (1999), pp. 325-336.

Ballew, J.T., "Antibody Biomarker Discovery Through in Vitro Directed Evolution of Consensus Recognition Epitopes," Proceedings of the National Academy of Sciences of the United States of America, Nov. 26, 2013, pp. 19330-19335, vol. 110, No. 48.

Buus, S. et al., "High-Resolution Mapping of Linear Antibody Epitopes Using Ultrahigh-Density Peptide Microarrays," Molecular & Cellular Proteomics, Dec. 2012, pp. 1790-1800, vol. 11, No. 12.

PCT/US2019/55245—International Search Report and Written Opinion, Mar. 4, 2020, 20 pages.

Choung et al., "Reactivity to Neoepitopes of DGP-TTG Complexes can Predict the Healing Status in Treated Celiac Patients." Gastroenterology 152, No. 5 (2017): S70, Abstract.

Di Pisa et al., "Synthetic Peptides Reproducing Tissue Transglutaminase-Gliadin Complex Neo-epitopes as Probes for Antibody Detection in Celiac Disease Patients' Sera." Journal of medicinal chemistry 58, No. 3 (2015): 1390-1399.

PCT/US2019/55249—Invitation to Pay Additional Fees, Jan. 8, 2020, 3 pages.

PCT/US2019/55249—International Preliminary Report on Patentability, Apr. 8, 2021, 13 pages.

PCT/US2015/49528—International Preliminary Report on Patentability, Sep. 27, 2016, 13 pages.

PCT/US2015/49528—International Search Report and Written Opinion, Feb. 1, 2016, 18 pages.

PCT/US2015/49528—Invitation to Pay Additional Fees, Nov. 20, 2015, 3 pages.

Choung et al., "578-Expanding Immune Reactivity Against Gliadin and TTG Epitopes Long Precedes Celiac Disease Diagnosis." Gastroenterology 154, No. 6 (2018): S-119.

Lytton et al., "Neo-epitope tissue transglutaminase autoantibodies as a biomarker of the gluten sensitive skin disease-dermatitis herpetiformis." Clinica Chimica Acta 415 (2013): 346-349.

Forsstrom B, Axnas BB, Stengele KP, et al. Proteome-wide epitope mapping of antibodies using ultra-dense peptide arrays. Mol Cell Proteomics 2014;13:1585-97.

Petersen, N., et al., "Fast and efficient characterization of an anti-gliadin monoclonal antibody epitope related to celiac disease using resin-bound peptides", Journal of Immunological Methods , vol. 365, 2011, 174-182.

Rubio-Tapia A, Hill ID, Kelly CP, et al. ACG clinical guidelines: diagnosis and management of Celiac disease. Am J Gastroenterol 2013; 108:656-76; quiz 677.

Jabri B, Sollid LM. T Cells in Celiac Disease. J Immunol 2017;198:3005-3014.

Sulkanen S, Halttunen T, Laurila K, et al. Tissue transglutaminase autoantibody enzyme-linked immunosorbent assay in detecting Celiac disease. Gastroenterology 1998; 115:1322-8.

Walker MM, Murray JA, Ronkainen J, et al. Detection of Celiac disease and lymphocytic enteropathy by parallel serology and histopathology in a population-based study. Gastroenterology 2010;139:112-9.

Cavell B, Stenhammar L, Ascher H, et al. Increasing incidence of childhood coeliac disease in Sweden. Results of a national study. Acta Paediatr 1992;81:589-92.

Ludvigsson JF, Lebwohl B, Green PH. Amount May Beat Timing: Gluten Intake and Risk of Childhood Celiac Disease. Clin Gastroenterol Hepatol 2016; 14:410-2.

Myleus A, Ivarsson A, Webb C, et al. Celiac disease revealed in 3% of Swedish 12-year-olds born during an epidemic. J Pediatr Gastroenterol Nutr 2009;49: 170-6.

Molberg O, McAdam S, Lundin KE, et al. T cells from Celiac disease lesions recognize gliadin epitopes deamidated in situ by endogenous tissue transglutaminase. Eur J Immunol 2001;31:1317-23.

Aleanzi M, Demonte AM, Esper C, et al. Celiac disease: antibody recognition against native and selectively deamidated gliadin peptides. Clin Chem 2001;47:2023-8.

Sollid LM, Molberg O, McAdam S, et al. Autoantibodies in coeliac disease: tissue transglutaminase—guilt by association? Gut 1997;41:851-2.

Matthias T, Neidhofer S, Pfeiffer S, et al. Novel trends in Celiac disease. Cell Mol Immunol 2011;8:121-5.

Bizzaro N, Tozzoli R, Villalta D, et al. Cutting-edge issues in Celiac disease and in gluten intolerance. Clin Rev Allergy Immunol 2012;42:279-87.

Lebwohl B, Murray JA, Rubio-Tapia A, et al. Predictors of persistent villous atrophy in coeliac disease: a population-based study. Aliment Pharmacol Ther 2014;39:488-95.

Breiman L. Random Forests. Machine Learning 2001;45:5-32.

Renard BY, Lower M, Kuhne Y, et al. rapmad: Robust analysis of peptide microarray data. BMC Bioinformatics 2011;12:324.

Pedregosa F, Varoquaux G, Gramfort A, et al. Scikit-learn: Machine Learning in Python. Journal of Machine Learning Research 2011;12:2825-2830.

Hilsenbeck SG, Friedrichs WE, Schiff R, et al. Statistical analysis of array expression data as applied to the problem of tamoxifen resistance. J Natl Cancer Inst 1999;91:453-9.

Ciccocioppo R, Di Sabatino A, Ara C, et al. Gliadin and tissue transglutaminase complexes in normal and coeliac duodenal mucosa. Clin Exp Immunol 2003;134:516-24.

Van der Windt DA, Jellema P, Mulder CJ, et al. Diagnostic testing for Celiac disease among patients with abdominal symptoms: a systematic review. JAMA 2010;303:1738-46.

Health Quality O. Clinical utility of serologic testing for Celiac disease in ontario: an evidence-based analysis. Ont Health Technol Assess Ser 2010;10:1-111.

Rashtak S, Ettore MW, Homburger HA, et al. Combination testing for antibodies in the diagnosis of coeliac disease: comparison of multiplex immunoassay and ELISA methods. Aliment Pharmacol Ther 2008;28:805-13.

Sugai E, Selvaggio G, Vazquez H, et al. Tissue transglutaminase antibodies in Celiac disease: assessment of a commercial kit. Am J Gastroenterol 2000;95:2318-22.

Hopper AD, Hadjivassiliou M, Hurlstone DP, et al. What is the role of serologic testing in Celiac disease? A prospective, biopsy-confirmed study with economic analysis. Clin Gastroenterol Hepatol 2008;6:314-20.

Husby S, Koletzko S, Korponay-Szabo IR, et al. European Society for Pediatric Gastroenterology, Hepatology, and Nutrition guidelines for the diagnosis of coeliac disease. J Pediatr Gastroenterol Nutr 2012;54:136-60.

Ludvigsson JF, Bai JC, Biagi F, et al. Diagnosis and management of adult coeliac disease: guidelines from the British Society of Gastroenterology. Gut 2014;63:1210-28.

Ludvigsson JF, Agreus L, Ciacci C, et al. Transition from childhood to adulthood in coeliac disease: the Prague consensus report. Gut 2016;65:1242-51.

Bai JC, Ciacci C, Corazza GR, et al. World Gastroenterology Organisation Practice Guidelines:Celiac Disease; World Gastroenterology Organisation: Milwaukee, WI, USA. 2016:1-35.

Skovbjerg H, Koch C, Anthonsen D, et al. Deamidation and cross-linking of gliadin peptides by transglutaminases and the relation to Celiac disease. Biochim Biophys Acta 2004;1690:220-30.

Matthias T, Pfeiffer S, Selmi C, et al. Diagnostic challenges in Celiac disease and the role of the tissue transglutaminase-neo-epitope. Clin Rev Allergy Immunol 2010;38:298-301.

Porcelli B, Ferretti F, Vindigni C, et al. Assessment of a Test for the Screening and Diagnosis of Celiac Disease. J Clin Lab Anal 2016;30:65-70.

(56) References Cited

OTHER PUBLICATIONS

Lebwohl B, Granath F, Ekbom A, et al. Mucosal healing and risk for lymphoproliferative malignancy in Celiac disease: a population-based cohort study. Ann Intern Med 2013;159:169-75.

Lebwohl B, Michaelsson K, Green PH, et al. Persistent mucosal damage and risk of fracture in Celiac disease. J Clin Endocrinol Metab 2014;99:609-16.

Rubio-Tapia A, Rahim MW, See JA, et al. Mucosal recovery and mortality in adults with Celiac disease after treatment with a gluten-free diet. Am J Gastroenterol 2010; 105:1412-20.

Lebwohl B, Granath F, Ekbom A, et al. Mucosal healing and mortality in coeliac disease. Aliment Pharmacol Ther 2013;37:332-9.

Rostom A, Murray JA, Kagnoff MF. American Gastroenterological Association (AGA) Institute technical review on the diagnosis and management of Celiac disease. Gastroenterology 2006;131:1981-2002.

Institute Aga. Aga Institute Medical Position Statement on the Diagnosis and Management of Celiac Disease. Kagnoff, Martin F. Gastroenterology 2006;131:1977-80.

Leonard MM, Weir DC, DeGroote M, et al. Value of IgA tTG in Predicting Mucosal Recovery in Children With Celiac Disease on a Gluten-Free Diet. J Pediatr Gastroenterol Nutr 2017;64:286-291.

Silvester JA, Kurada S, Szwajcer A, et al. Tests for Serum Transglutaminase and Endomysial Antibodies Do Not Detect Most Patients With Celiac Disease and Persistent Villous Atrophy on Gluten-free Diets: a Meta-analysis. Gastroenterology 2017;153:689-701 e1.

Lanzini A, Lanzarotto F, Villanacci V, et al. Complete recovery of intestinal mucosa occurs very rarely in adult coeliac patients despite adherence to gluten-free diet. Aliment Pharmacol Ther 2009;29:1299-308.

Kaukinen K, Collin P, Laurila K, et al. Resurrection of gliadin antibodies in coeliac disease. Deamidated gliadin peptide antibody test provides additional diagnostic benefit. Scand J Gastroenterol 2007;42:1428-33.

Volta U, Granito A, Fiorini E, et al. Usefulness of antibodies to deamidated gliadin peptides in Celiac disease diagnosis and follow-up. Dig Dis Sci 2008;53:1582-8.

Spatola BN, Kaukinen K, Collin P, et al. Persistence of elevated deamidated gliadin peptide antibodies on a gluten-free diet indicates nonresponsive coeliac disease. Aliment Pharmacol Ther 2014;39:407-17.

Monzani A, Rapa A, Fonio P, et al. Use of deamidated gliadin peptide antibodies to monitor diet compliance in childhood Celiac disease. J Pediatr Gastroenterol Nutr 2011;53:55-60.

McRae BL, Vanderlugt CL, Dal Canto MC, et al. Functional evidence for epitope spreading in the relapsing pathology of experimental autoimmune encephalomyelitis. J Exp Med 1995;182:75-85.

Lehmann PV, Forsthuber T, Miller A, et al. Spreading of T-cell autoimmunity to cryptic determinants of an autoantigen. Nature 1992;358:155-7.

Sohnlein P, Muller M, Syren K, et al. Epitope spreading and a varying but not disease-specific GAD65 antibody response in Type I diabetes. The Childhood Diabetes in Finland Study Group. Diabetologia 2000;43:210-7.

Vincent A, Willcox N, Hill M, et al. Determinant spreading and immune responses to acetylcholine receptors in myasthenia gravis. Immunol Rev 1998;164:157-68.

Vanderlugt CL, Miller SD. Epitope spreading in immune-mediated diseases: implications for immunotherapy. Nat Rev Immunol 2002;2:85-95.

Sivalingam GN, Shepherd AJ. An analysis of B-cell epitope discontinuity. Mol Immunol 2012;51:304-9.

Reineke, U., et al., A synthetic mimic of a discontinuous binding site on interleukin-10, Nat. Biotech., 1999, 17:271-275.

Reineke, U. et al., Epitope Mapping Protocols, Second Edition, Methods in Molecular Biology 524, Springer Protocols, 7 pages. Appendix A of U.S. Appl. No. 61/761,347.

\* cited by examiner

Figure 2B:
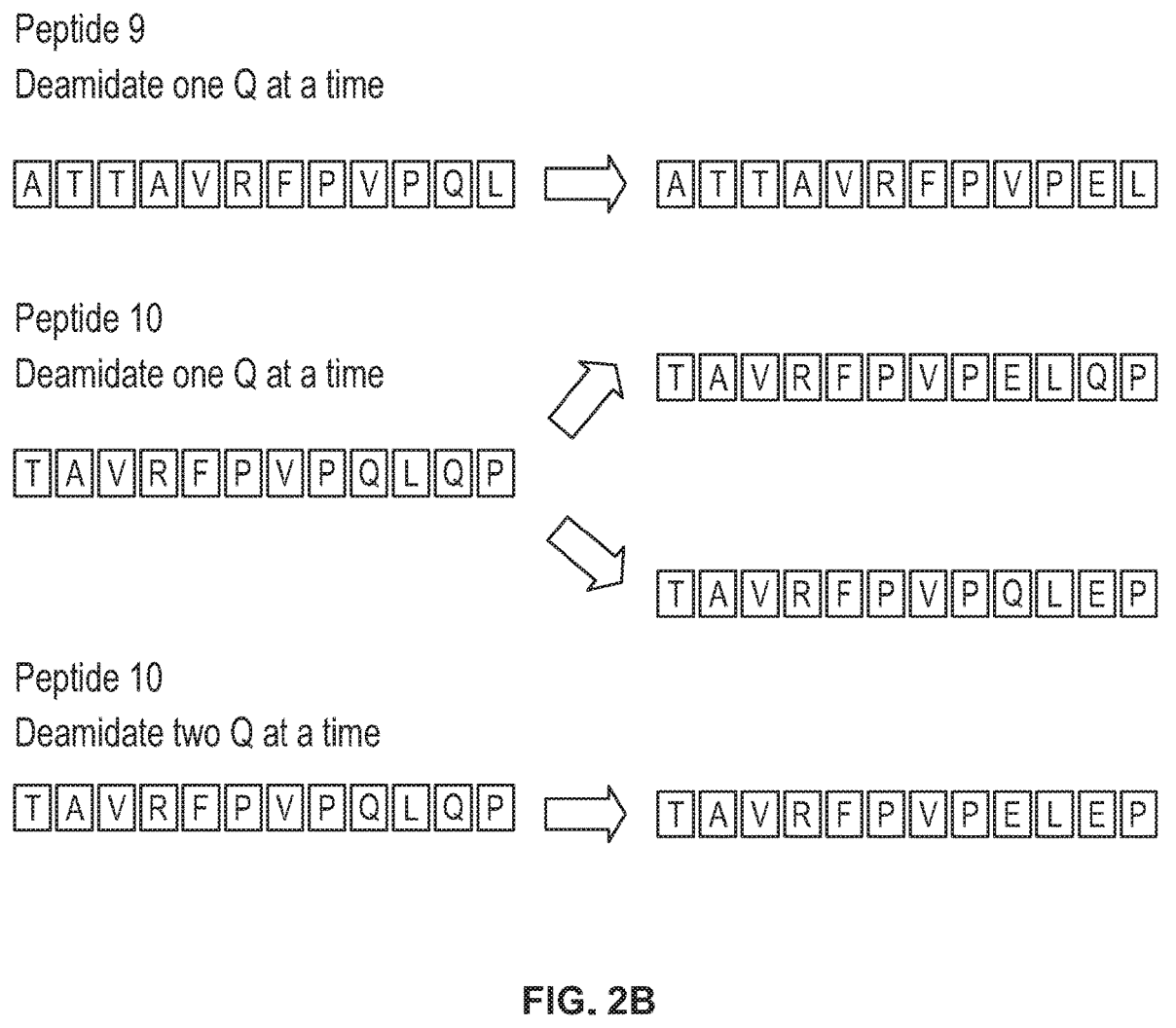

Peptide 9

Deamidate one Q at a time

A T T A V R F P V P Q L ⟹ A T T A V R F P V P E L

Peptide 10

Deamidate one Q at a time

T A V R F P V P Q L Q P ⟹ T A V R F P V P E L Q P

T A V R F P V P Q L E P

Peptide 10

Deamidate two Q at a time

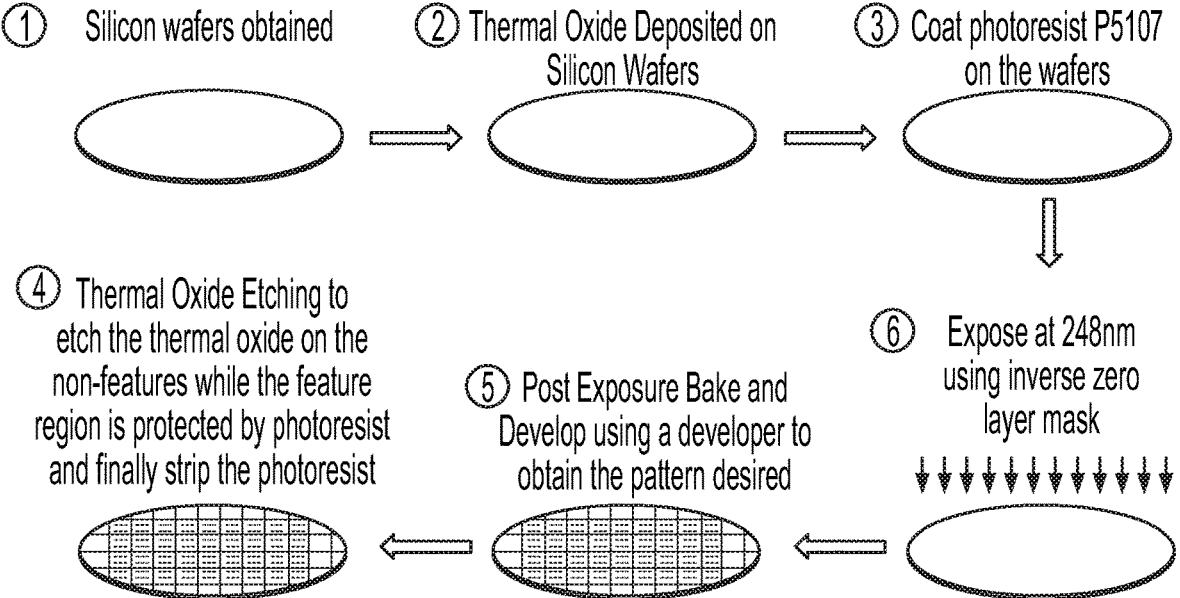

① Silicon wafers obtained          ② Thermal Oxide Deposited on Silicon Wafers          ③ Coat photoresist P5107 on the wafers ④ Thermal Oxide Etching to etch the thermal oxide on the non-features while the feature region is protected by photoresist and finally strip the photoresist ⑤ Post Exposure Bake and Develop using a developer to obtain the pattern desired ⑥ Expose at 248nm using inverse zero layer mask

FIG. 3A

Binding
intensity 0    100

Healthy
Controls

Untreated
Biopsy
Proven CD

Treated/
**Unhealed
CD**

Treated/
**Healed
CD** tTG-DGP BIOMARKERS FOR MONITORING CELIAC DISEASE

CROSS REFERENCE TO RELATED APPLICATIONS

This application is a U.S. National Phase Application of International Application No. PCT/US19/55249, filed Oct. 8, 2019, which claims the benefit of U.S. Provisional Application No. 62/742,863, filed Oct. 8, 2018, each of which is hereby incorporated in its entirety by reference.

SEQUENCE LISTING

The instant application contains a Sequence Listing which has been submitted electronically in ASCII format and is hereby incorporated by reference in its entirety. Said ASCII copy, created on Nov. 12, 2019, is named VIB-011WO_SL.txt and is 49,101 bytes in size.

BACKGROUND

Celiac disease (CeD) has the features of an autoimmune disease such as increased antibody levels to the self-antigen tissue transglutaminase (tTG) that return to normal when adhering to a gluten-free diet (GFD).[1] Although a GFD is an effective therapy for CeD, patients with CeD frequently find it difficult to adhere to a GFD, resulting in ongoing intestinal damage. Several studies have shown that persistent mucosal damage in patients with treated CeD mucosa was associated with several severe complications, including lymphoprolif-erative malignancy, bone diseases,[34, 35] and possibly excess mortality.[36, 37] Similar to other chronic conditions, disease monitoring in patients with treated CeD mucosa is necessary.

Serologic tests for CeD have been extensively investi-gated and are considered an effective first step in diagnosing and monitoring CeD.[5, 21-25] Currently, the primary serologic markers of CeD are antibodies to tTG and gliadin peptides (GPs) that have been deamidated by tTG.[4, 5] Recent Euro-pean guidelines suggested that sufficiently and strongly positive serologic tests for CeD, including tests for tTG-IgA and endomysial antibody, are enough to confirm CeD; therefore, biopsy of the small intestines may not be needed to diagnose CeD in this subgroup.[26] However, the results of serologic tests vary greatly across different settings and populations,[5, 23 ,25] and are not well correlated with intesti-nal mucosal healing status in patients with treated CeD.[40, 41] In particular, the positive predictive values of CeD serologic tests are relatively low because of the low prevalence of CeD. In addition, tTG-IgA test is not effective to diagnose CeD in patients with selective IgA deficiency, which are more commonly associated with CeD than in the general population. A recent meta-analysis reported that serologic tests for CeD, including tests for tTG-IgA and endomysial antibody, have low sensitivity (less than 50%) compared with follow-up biopsy for detecting persistent villous atro-phy in patients with CeD who adhere to a GFD. Compared to tTG-IgA, deamidated gliadin peptide (DGP)-IgA has been shown to better identify the healing status in treated CeD patients, but the sensitivity and specificity of DGP-IgA were not optimal. Due to this variability in CeD serology, biopsy of the small intestines is still considered the definitive method for diagnosing CeD and verifying intestinal heal-ing.[14] However, biopsy is both invasive and expensive. Therefore, there is a need for more accurate noninvasive markers for monitoring CeD.

SUMMARY

The present invention relates to the field of identification of biomarkers for CeD. More specifically, the present inven-tion relates to the field of identification of neoepitopes derived from tTG-DGP complexes as biomarkers for diag-nosis of CeD, and for determination of healing status of patients diagnosed with CeD. The identified neoepitopes of the tTG-DGP complex show comparable or even higher diagnostic accuracy for discriminating CeD than clinically available serologic tests. Furthermore, these neoepitopes identify healing status in patients with treated CeD with much higher sensitivity and specificity than current sero-logic tests. Therefore, these neoepitopes can be used as indicators of persistent mucosal injury in patients with treated CeD, thereby avoiding expensive and invasive intes-tinal biopsies.

In one aspect, the invention provides an array that com-prises an array surface and at least two peptide probes. Each of the at least two peptide probes comprises a binding motif selected from the group consisting of SEQ ID NOS: 1-172. The peptide probes extend from the array surface.

The array surface can comprise any type of surface. For instance, in some embodiments, the array surface can be a solid surface. In such embodiments, the solid surface can be a microparticle.

In certain embodiments, the at least two peptide probes are capable of binding to an antibody associated with Celiac disease. In some embodiments, the at least two peptide probes can further include a label.

In another aspect, the invention provides an array of features attached to a surface at positionally-defined loca-tions. The features include at least one engineered polypep-tide chain. The engineered polypeptide chain includes at least two epitope sequences from a bioactive polypeptide, and at least one epitope sequence from a protein. The bioactive polypeptide generates an immune response in a subject having Celiac disease. The protein binds to antibod-ies of the subject having Celiac disease.

The bioactive polypeptide can be selected from the group consisting of alpha gliadin, beta gliadin, gamma gliadin, omega gliadin, and other wheat-related proteins or peptides. The protein that binds to antibodies of the subject having Celiac disease can be tissue transglutaminase (tTG). In certain embodiments, the engineered polypeptide chain can include at least 1, 2, 3, 4, 5, 6, 7, 8, 9, 10, 20, 30, 40, 50, 60, 70, 80, 90, or 100 sequences selected from the group consisting of SEQ ID NOS: 1-172. In further embodiments, the engineered polypeptide chain can further include at least one randomly generated polypeptide sequence.

The features attached to the surface at the positionally-defined locations can be any length of amino acids. In certain embodiments, the features attached to the surface at positionally-defined locations can be from 6-15 amino acids in length. In more particular embodiments, the features attached to the surface at positionally-defined locations can be 12 amino acids in length.

Similarly, the epitope sequences that comprise the fea-tures attached to the surface can be any length of amino acids. For instance, in some embodiments, each of the at least two epitope sequences from the bioactive polypeptide can consist of 3, 4, 5, 6, 7, 8, 9, 10, or 11 amino acids. In more particular embodiments, each of the at least two epitope sequences from the bioactive polypeptide can con-sist of three amino acids.

In certain embodiments, the features attached to the surface can be configured to have at least 90% sensitivity and 90% specificity for detection of Celiac disease after contact of the features with a sample from a subject suspected of having Celiac disease. In further embodiments in which the at least one engineered polypeptide chain is 12 amino acids in length, and each of the at least two epitope sequences from the bioactive polypeptide comprising the polypeptide chain consists of 3 amino acids, each of the at least two epitope sequences from the bioactive polypeptide can have at least 20% sensitivity for binding to an antibody in a Celiac positive sample.

The array of features can include at least 10,000 features in certain embodiments. In such embodiments, each feature can be attached to a surface of the array at a different positionally-defined location that corresponds to a positionally-defined location of a pillar having a top surface of at least 1 $\mu m^2$ in size. In such embodiments, each feature of the array can further comprise a different engineered peptide chain compared to the other features of the array. Furthermore, each feature can comprise at least 500 identical full-length, where each identical full-length peptide chain has an engineered full-length of at least 7 amino acids in length. In such embodiments, the purity of each feature with regards to the fraction of full-length engineered peptide chains can be a fraction F of the full-length engineered peptide chains of each feature having a engineered sequence and a engineered full-length sequence length N being characterized by $F=10^{(N+1)-log\ (E/110\%)}$ with an average coupling efficiency E of at least 98.5% for coupling each amino acid of the engineered sequence, and the sequence length N being at least 7 amino acids in length, the fraction of the less than full-length engineered peptide chains equaling (1-F). In even further embodiments, the surface of the array can be a substrate, and the substrate can comprise a planar layer having an upper surface and a lower surface. The substrate can also have a plurality of pillars operatively coupled to the layer in the positionally-defined locations. Each pillar can have a planar surface extended from the layer, such that the distance between the surface of each pillar and the upper surface of the layer is between 1,000-5,000 angstroms, and such that the plurality of pillars are present at a density of greater than 10,000/$cm^2$.

In yet another aspect, the invention provides a method of detecting healing status in a subject that has Celiac disease. The method includes obtaining a sample from the subject that in part comprises subject antibodies, contacting an array of synthetic polypeptides with the subject sample, identifying an antibody-binding intensity value for each of the synthetic polypeptides in the array, and determining a healing status of the subject based on the identified antibody-binding intensity values for each of the synthetic polypeptides in the array. In such embodiments, each synthetic polypeptide in the array comprises at least two epitope sequences from a bioactive polypeptide that generates an immune response in subjects having Celiac disease and at least one epitope sequence from a protein that binds to the subject antibodies.

The bioactive polypeptide can be selected from the group consisting of: alpha gliadin, beta gliadin, gamma gliadin, and omega gliadin. Furthermore, at least one of the two epitope sequences from the bioactive polypeptide can comprise a deamidated polypeptide sequence. Additionally, the at least two epitope sequences from the bioactive polypeptide can be discontinuous in the bioactive polypeptide. In certain embodiments, each of the at least two epitope sequences from the bioactive polypeptide can be three amino acids in length.

The protein that binds to the subject antibodies can comprise tissue transglutaminase in certain embodiments. The subject antibodies can be IgA and/or IgG antibodies. Alternatively, in some embodiments, the subject can be IgA deficient. The subject can, in certain embodiments, adhere to a gluten free diet.

The synthetic polypeptides in the array can include one or more of the sequences selected from the group consisting of SEQ ID NOS: 1-172. In some embodiments, each synthetic polypeptide can further comprise at least one randomly generated polypeptide sequence. Furthermore, each synthetic polypeptides can be 12 amino acids in length. In certain embodiments, the synthetic polypeptides of the array can be configured to have at least 90% sensitivity and 90% specificity for detection of Celiac disease after the microarray has been contacted with the subject sample. In alternative embodiments, the synthetic polypeptides of the array can be configured to have at least 80% sensitivity and 90% specificity for detecting healing status in subjects having Celiac disease and adhering to a gluten free diet. The array of synthetic polypeptides can be a fluorescent array.

In certain embodiments, to identify an antibody-binding intensity value for each of the synthetic polypeptides in the array, the array can be imaged after the array has been contacted with the subject sample. Additionally, a fluorescence emission value for each of the synthetic polypeptides can be identified. Then, an antibody-binding intensity value for each of the synthetic polypeptides can be identified based on the identified fluorescence emission values.

In yet another aspect, the invention provides a method for identifying synthetic polypeptides for detecting healing status in a subject having Celiac disease. The method includes estimating the antibody-binding intensity of an array of synthesized tTG-DGP neoepitopes such that antibody-binding intensity values are linked to corresponding peptide sequences. The method further includes eliminating background noise using background normalization modeling performed with an expectation-maximization algorithm. The method further includes applying vector machine modeling to a training set of peptides to construct a hyperplane and maximize the margins of the training data between the 2 classes (Celiac disease vs no Celiac disease), such that a set of disease-associated peptide sequences of the tTG-DGP complex are determined. Then, the method incudes determining the sensitivity and specificity of each peptide identified as a disease-associated peptide sequence of the tTG-DGP complex, and identifying a further set of immunogenic epitopes of the tTG-DGP complex based on the sensitivity, specificity, and predictability of Celiac disease associated with the peptides in the set.

In yet another aspect, the invention provides an array for detecting healing status in a subject having Celiac disease. In some embodiments, the array includes synthetic polypeptides identified according to the method for identifying synthetic polypeptides described above. In alternative embodiments, the array includes one or more of the sequences selected from the group consisting of SEQ ID NOS: 1-172.

In yet another aspect, the invention provides an array of features attached to a surface at positionally-defined locations. In such embodiments, the array can include synthetic polypeptides identified according to the method for identifying synthetic polypeptides described above. In alternative embodiments, the array can include one or more of the sequences selected from the group consisting of SEQ ID NOS: 1-172.

5
6

In yet another aspect, the invention provides a method of identifying an autoimmune disorder in a subject. The method includes contacting a sample from the subject with any of the arrays disclosed above, and analyzing binding of antibodies in the sample to features on the array to determine whether the subject has the autoimmune disorder.

In some embodiments, the autoimmune disease can be Celiac disease. The method can provide a sensitivity of detection of the autoimmune disorder of at least 90%, 91%, 92%, 93%, 94%, 95%, 96%, 97%, 98%, or 99% in some embodiments. Additionally, the method can provide a specificity of detection of the autoimmune disorder least 90%, 91%, 92%, 93%, 94%, 95%, 96%, 97%, 98%, or 99% in some embodiments.

In yet another aspect, the invention provides a substantially purified and/or recombinant peptide comprising an amino acid sequence selected from the group consisting of SEQ ID NOS: 1-172, or a biologically active fragment or variant of any one or more thereof.

In yet another aspect, the invention provides a method of treating Celiac disorder or a Celiac related disorder in a patient. In such aspects, the method includes administering to the patient a formulation comprising an amino acid sequence selected from the group consisting of SEQ ID NOS: 1-127, or a biologically active fragment or variant of any one or more thereof.

In yet another aspect, the invention provides a method for determining the degree of Celiac disorder or a Celiac related disorder in a patient. In such aspects, the method includes measuring a reactivity of a serum sample of the patient contacted by a formulation comprising an amino acid sequence selected from the group consisting of SEQ ID NOS: 1-172, or a biologically active fragment or variant of any one or more thereof.

In yet another aspect, the invention provides a biomarker for Celiac disease that comprises a polypeptide epitope for a Celiac antibody. The polypeptide epitope is selected from the group consisting of SEQ ID NOS: 1-172, or a biologically active fragment or variant of any one or more thereof.

In yet another aspect, the invention provides an agent that comprises one or more of the biomarkers for Celiac disease discussed above.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale; the size and relative sizes of components may be exaggerated for clarity. Like numbers refer to like elements throughout. In the drawings:

FIG. 2A discloses SEQ ID NO: 176 (peptide 1, MKTFLILVLLAT), SEQ ID NO: 177 (peptide 2, TFLILVLLATIV), SEQ ID NO: 178, peptide 3, LILVLLATIVAT), SEQ ID NO: 179 (peptide 4, LVLLATIVATAT), SEQ ID NO: 180 (peptide 5, LLATIVATATTA), SEQ ID NO: 181 (peptide 6, ATIVATATTAVR), SEQ ID NO: 182 (peptide 7, IVATATTAVRFP), SEQ ID NO: 183 (peptide 8, ATATTAVRFPVP), SEQ ID NO: 184

(peptide 9, ATTAVRFPVPQL), SEQ ID NO: 185 (peptide 10, TAVRFPVPQLQP), SEQ ID NO: 186 (peptide 11, VRFPVPQLQPQN), and SEQ ID NO: 187 (peptide 143, CTIAPFGIFGTN).

FIG. 2B illustrates deamidation of 12-mer GPs, in accordance with an embodiment. FIG. 2B discloses SEQ ID NO: 184 (ATTAVRFPVPQL), SEQ ID NO: 188 (ATTAVRFPV-PEL), SEQ ID NO: 185 (TAVRFPVPQLQP), SEQ ID NO: 189 (TAVRFPVPELQP), SEQ ID NO: 190 (TAVRFPVPQ-LEP), and SEQ ID NO: 191 (TAVRFPVPELEP).

FIG. 3A illustrates wafer substrate preparation, in accordance with an embodiment.

Figure 3B:
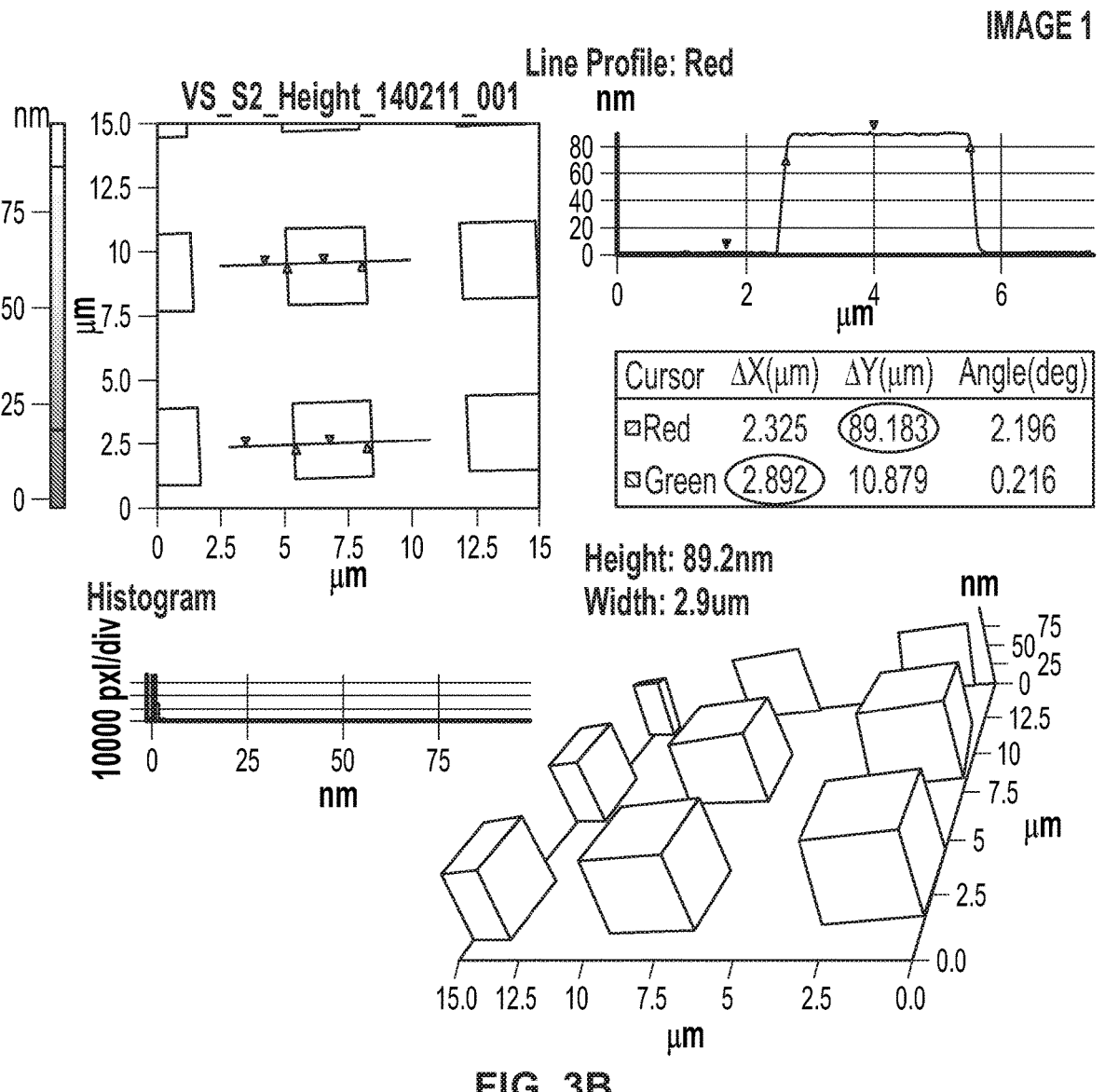

FIG. 3B illustrates pillars of a substrate, in accordance with an embodiment.

Figure 3C:
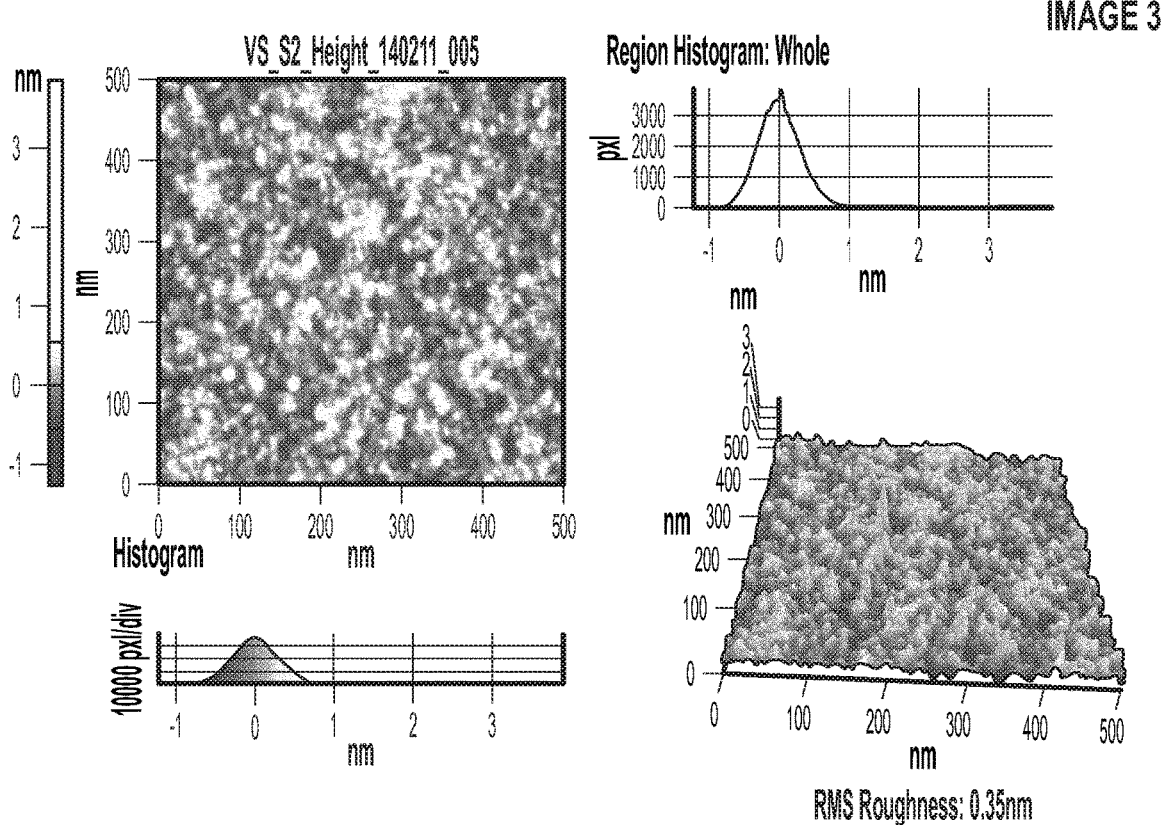

FIG. 3C illustrates AFM-measured roughness and calculated density of substrate, in accordance with an embodiment.

Figure 4:
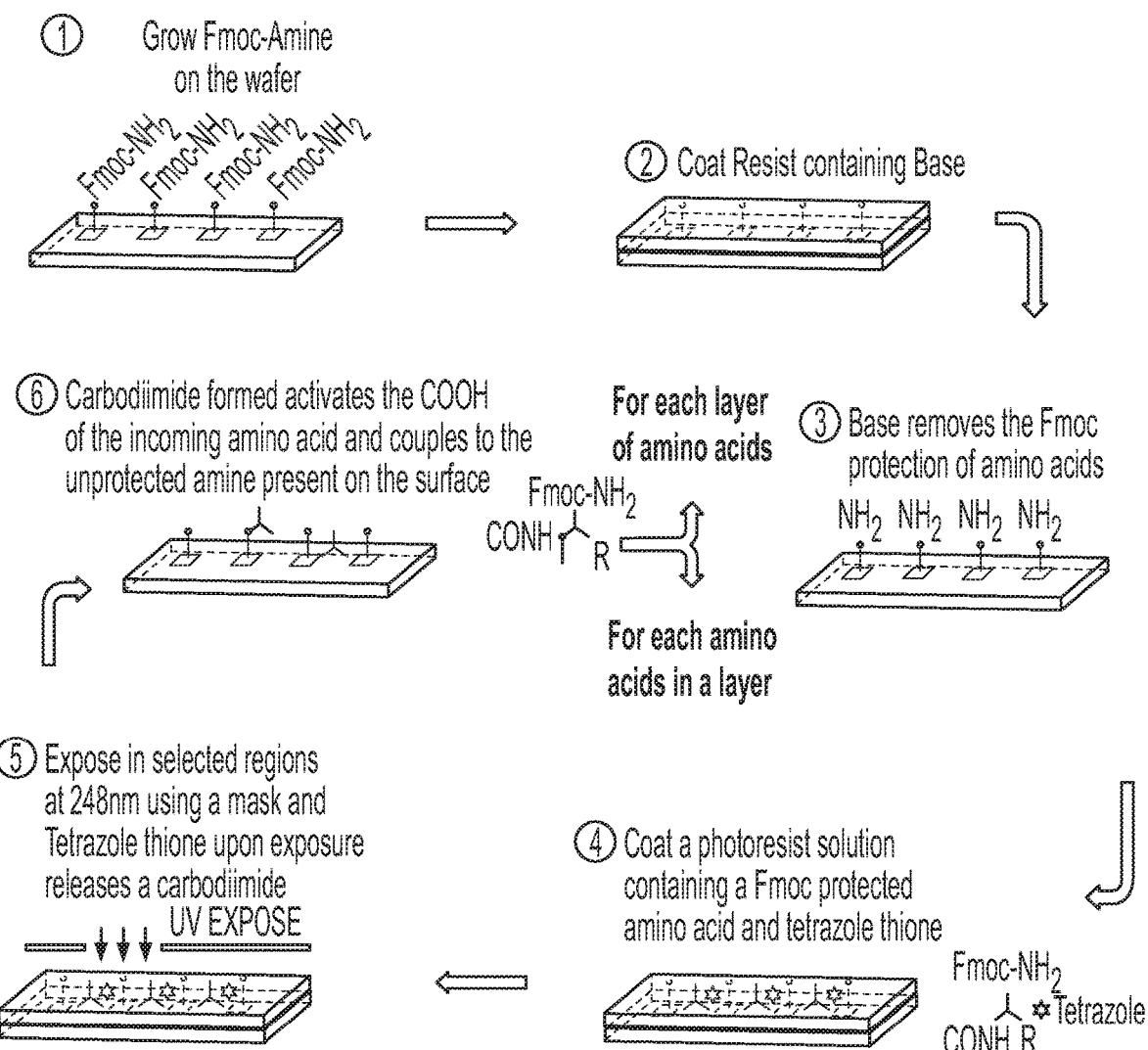

FIG. 4 illustrates peptide array synthesis, in accordance with an embodiment.

Figure 5:
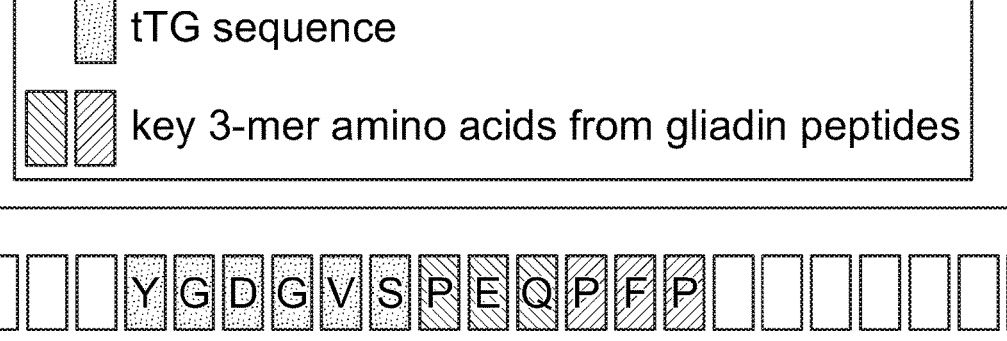

FIG. 5 is depicts examples of combined epitopes of the tTG-DGP complex, in accordance with an embodiment. FIG. 5 discloses SEQ ID NO: 192 (YGDGVSPEQPFP), SEQ ID NO: 193 (PEQYGDGVSPEP), and SEQ ID NO: 194 (PEQPEPYGDGVS).

Figure 6:
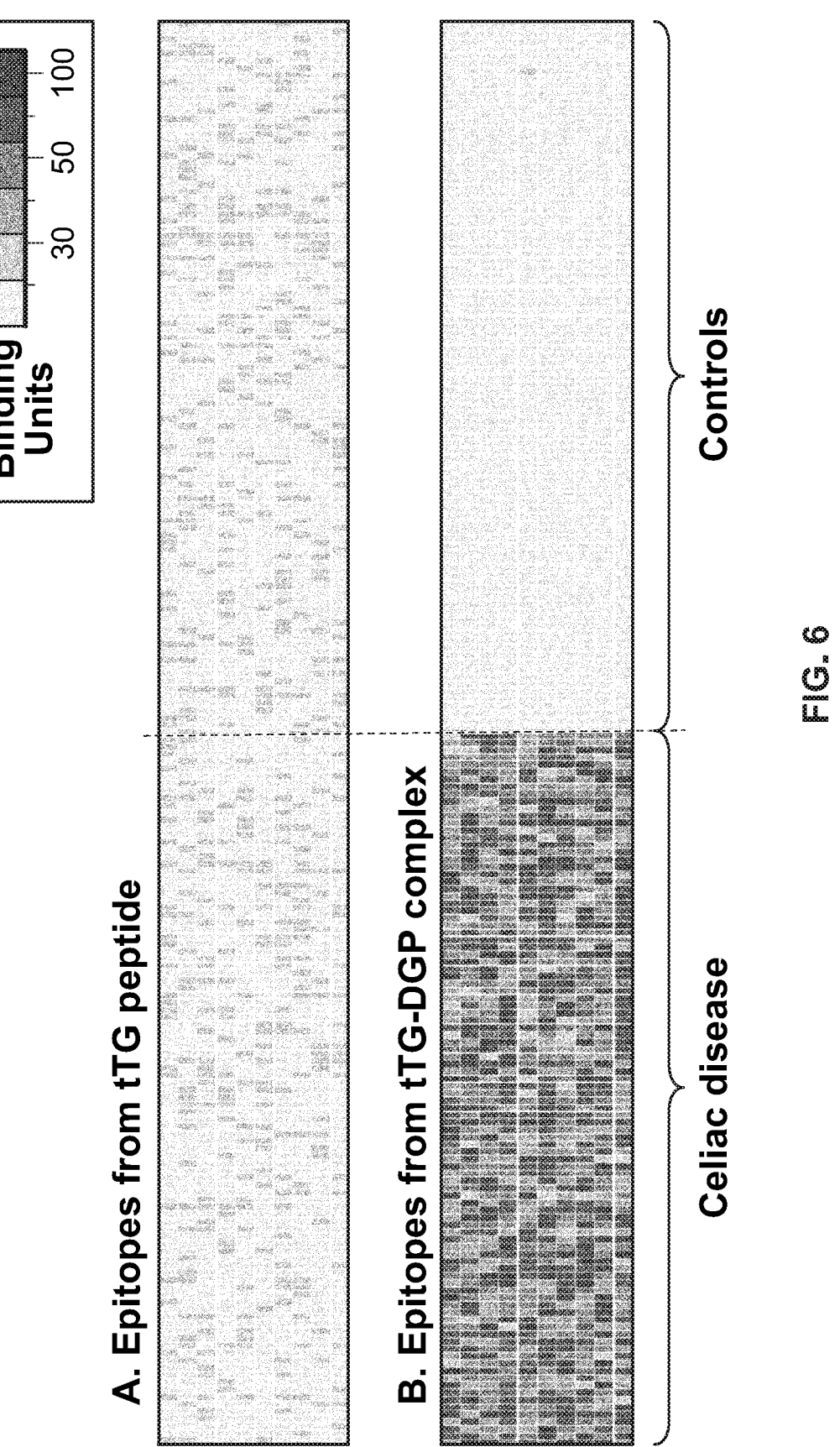

FIG. 6A depicts immune reactivity against the tTG peptide, in accordance with an embodiment.

FIG. 6B depicts immune reactivity against the neoepitopes of the tTG-DGP complex, in accordance with an embodiment.

Figure 7A:
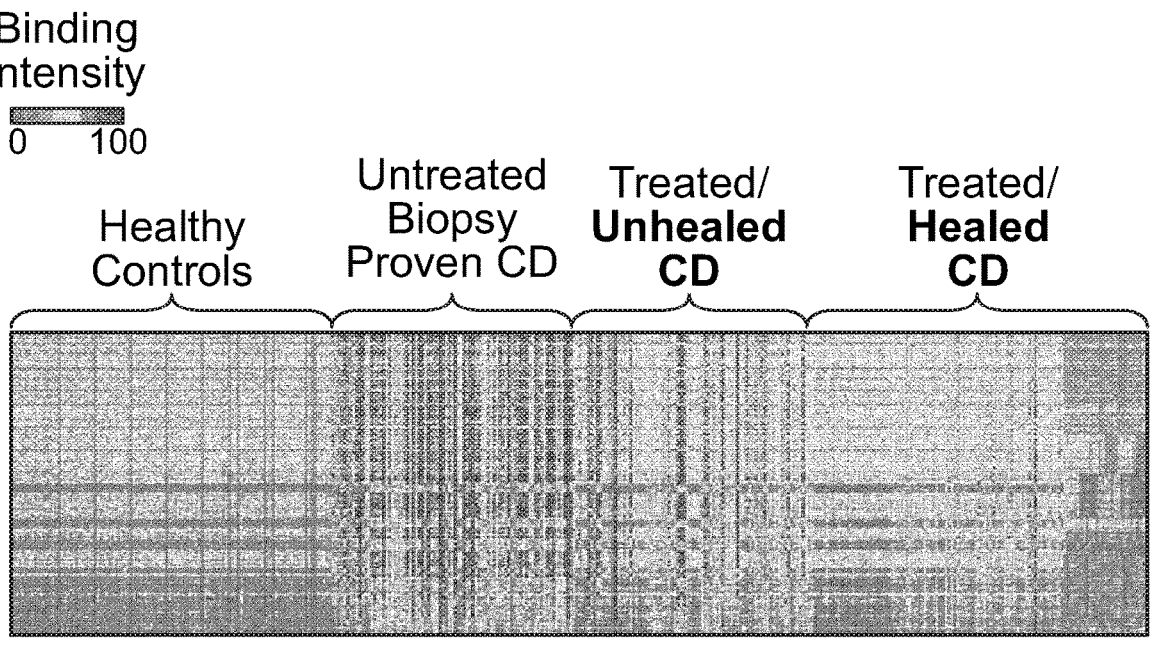

FIG. 7A depicts immune reactivity against epitopes of the tTG-DGP complex in patients with untreated CeD, treated but unhealed CeD, and treated and healed CeD, and in healthy control patients, in accordance with an embodiment.

Figure 7B:
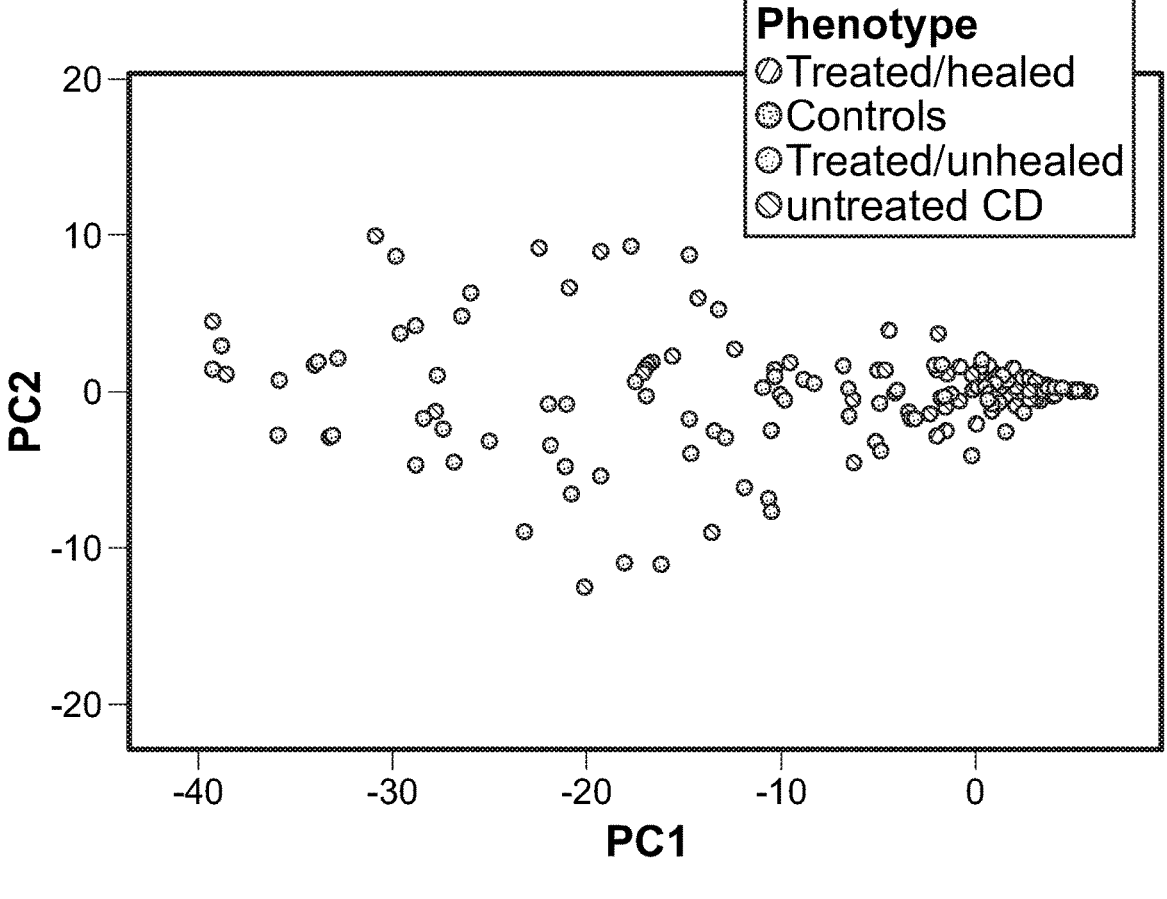

FIG. 7B depicts principal component analysis of immune reactivity against neoepitopes of the tTG-DGP complex, in accordance with an embodiment.

Figure 8:
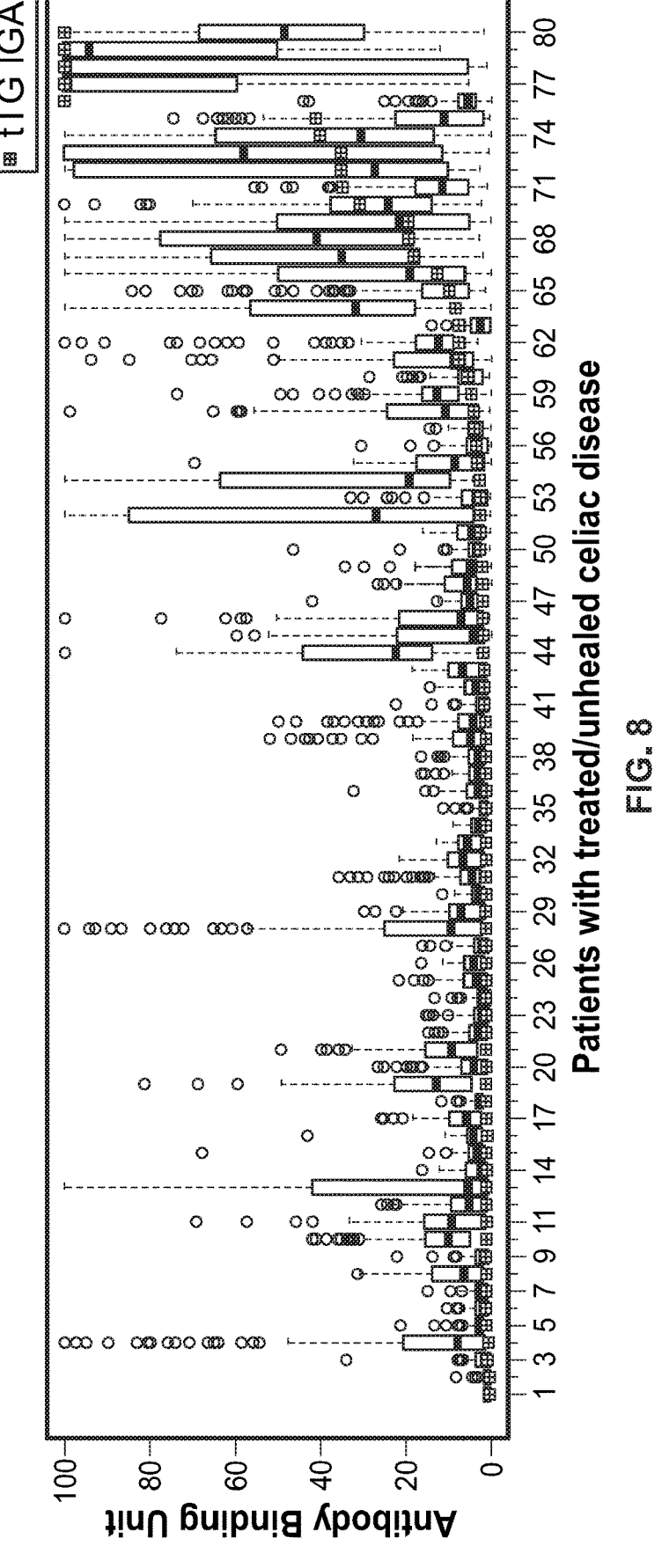

FIG. 8 depicts a comparison of antibody-binding levels of tTG-immunoglobulin A complex and antibody-binding levels of tTG-DGP complex in patients with treated but unhealed CeD, in accordance with an embodiment.

One skilled in the art will readily recognize from the following discussion that alternative embodiments of the structures and methods illustrated herein may be employed without departing from the principles of the invention described herein.

DETAILED DESCRIPTION

Definitions

Terms used in the claims and specification are defined as set forth below unless otherwise specified.

As used herein the term "wafer" refers to a slice of semiconductor material, such as silicon or a germanium crystal generally used in the fabrication of integrated circuits. Wafers can be in a variety of sizes from, e.g., 25.4 mm (1 inch) to 300 mm (11.8 inches) along one dimension with thickness from, e.g., 275 μm to 775 μm.

As used herein the term "photoresist" or "resist" or "photoactive material" refers to a light-sensitive material that changes its solubility in a solution when exposed to ultra violet or deep ultra violet radiation. Photoresists are organic or inorganic compounds that are typically divided into two types: positive resists and negative resists. A positive resist is a type of photoresist in which the portion of the photoresist that is exposed to light becomes soluble to the photoresist developer. The portion of the photoresist that is unexposed remains insoluble to the photoresist developer. A negative resist is a type of photoresist in which the portion of the photoresist that is exposed to light becomes insoluble to the photoresist developer. The unexposed portion of the photoresist is dissolved by the photoresist developer.

As used herein the term "photomask" or "reticle" or "mask" refers to an opaque plate with transparent patterns or holes that allow light to pass through. In a typical exposing process, the pattern on a photomask is transferred onto a photoresist.

As used herein the term "coupling molecule" or "monomer molecule" includes any natural or artificially synthesized amino acid with its amino group protected with a fluorenylmethyloxycarbonyl group or a t-butoxycarbonyl group. These amino acids may have their side chains protected as an option. Examples of coupling molecules include Boc-Gly-Oh, Fmoc-Trp-Oh. Other examples are described below.

As used herein the term "coupling" or "coupling process" or "coupling step" refers to a process of forming a bond between two or more molecules such as a linking molecule or a coupling molecule. A bond can be a covalent bond such as a peptide bond. A peptide bond can be a chemical bond formed between two molecules when the carboxyl group of one coupling molecule reacts with the amino group of the other coupling molecule, releasing a molecule of water ($H_2O$). This is a dehydration synthesis reaction (also known as a condensation reaction), and usually occurs between amino acids. The resulting CO—NH bond is called a peptide bond, and the resulting molecule is an amide.

As used herein the terms "biomolecule," "polypeptide," "peptide," or "protein" are used interchangeably to describe a chain or polymer of amino acids that are linked together by bonds. Accordingly, the term "peptide" as used herein includes a dipeptide, tripeptide, oligopeptide, and polypeptide. The term "peptide" is not limited to any particular number of amino acids. In some embodiments, a peptide contains about 2 to about 50 amino acids, about 5 to about 40 amino acids, about 5 to about 20 amino acids, or about 7 to about 15 amino acids. A molecule, such as a protein or polypeptide, including an enzyme, can be a "native" or "wild-type" molecule, meaning that it occurs naturally in nature; or it may be a "mutant," "variant," "derivative," or "modification," meaning that it has been made, altered, derived, or is in some way different or changed from a native molecule or from another molecule such as a mutant.

As used herein the term "linker molecule" or "spacer molecule" includes any molecule that does not add any functionality to the resulting peptide but spaces and extends out the peptide from the substrate, thus increasing the distance between the substrate surface and the growing peptide. This generally reduces steric hindrance with the substrate for reactions involving the peptide (including uni-molecular folding reactions and multi-molecular binding reactions) and so improves performance of assays measuring one or more embodiments of peptide functionality.

As used herein the term "developer" refers to a solution that can selectively dissolve the materials that are either exposed or not exposed to light. Typically developers are water-based solutions with minute quantities of a base added. Examples include tetramethyl ammonium hydroxide in water-based developers. Developers are used for the initial pattern definition where a commercial photoresist is used. Use of developers is described in Example 1 below.

As used herein the term "protecting group" includes a group that is introduced into a molecule by chemical modification of a functional group in order to obtain chemoselectivity in a subsequent chemical reaction. Chemoselectivity refers to directing a chemical reaction along a desired path to obtain a pre-selected product as compared to another. For example, the use of tboc as a protecting group enables chemoselectivity for peptide synthesis using a light mask and a photoacid generator to selectively remove the protecting group and direct pre-determined peptide coupling reactions to occur at locations defined by the light mask.

As used herein the term "microarrays" refers to a substrate on which different probe molecules of protein or specific DNA binding sequences have been affixed at separate locations in an ordered manner thus forming a microscopic array.

As used herein the term "microarray system" refers to a system usually comprised of biomolecular probes formatted on a solid planar surface like glass, plastic or silicon chip plus the instruments needed to handle samples (automated robotics), to read the reporter molecules (scanners) and analyze the data (bioinformatic tools).

As used herein the term "patterned region" or "pattern" or "location" refers to a region on the substrate on which are grown different features. These patterns can be defined using photomasks.

As used herein the term "derivatization" refers to the process of chemically modifying a surface to make it suitable for biomolecular synthesis. Typically derivatization includes the following steps: making the substrate hydrophilic, adding an amino silane group, and attaching a linker molecule.

As used herein the term "capping" or "capping process" or "capping step" refers to the addition of a molecule that prevents the further reaction of the molecule to which it is attached. For example, to prevent the further formation of a peptide bond, the amino groups are typically capped with an acetic anhydride molecule.

As used herein the term "diffusion" refers to the spread of a chemical through random motion from regions of higher concentration to regions of lower concentration.

As used herein the term "dye molecule" refers to a dye which typically is a colored substance that can bind to a substrate. Dye molecules can be useful in detecting binding between a feature on an array and a molecule of interest.

As used herein, the terms "immunological binding" and "immunological binding properties" refer to the type of non-covalent interactions that occurs between an immunoglobulin molecule (or variant thereof such as an scFv) and an antigen for which the immunoglobulin is specific.

As used herein the term "biological sample" refers to a sample derived from biological tissue or fluid that can be assayed for an analyte(s) of interest. Such samples include, but are not limited to, sputum, amniotic fluid, blood, blood cells (e.g., white cells), tissue or fine needle biopsy samples, urine, peritoneal fluid, and pleural fluid, or cells therefrom. Biological samples may also include sections of tissues such as frozen sections taken for histological purposes. Although the sample is typically taken from a human patient, the assays can be used to detect analyte(s) of interest in samples from any organism (e.g., mammal, bacteria, virus, algae, or yeast) or mammal, such as dogs, cats, sheep, cattle, and pigs. The sample may be pretreated as necessary by dilution in an appropriate buffer solution or concentrated, if desired.

As used herein, the term "assay" refers to a type of biochemical test that measures the presence or concentration of a substance of interest in solutions that can contain a complex mixture of substances.

The term "subject" includes inter alia an individual, patient, target, host or recipient regardless of whether the subject is a human or non-human animal including mammalian species and also avian species. The term "subject", therefore, includes a human, non-human primate (for example, gorilla, marmoset, African Green Monkey), livestock animal (for example, sheep, cow, pig, horse, donkey, goat), laboratory test animal (for example, rat, mouse, rabbit, guinea pig, hamster), companion animal (for example, dog, cat), captive wild animal (for example, fox, deer, game animals) and avian species including poultry birds (for example, chickens, ducks, geese, turkeys). The preferred subject, however, is a human.

The term "antigen" as used herein refers to a molecule that triggers an immune response by the immune system of a subject, e.g., the production of an antibody by the immune system and/or activation of the cellular arm of the immune system (e.g., activation of phagocytes, natural killer cells, and antigen-specific cytotoxic T-lymphocytes, along with release of various cytokines in response to an antigen). Antigens can be exogenous, endogenous or auto antigens. Exogenous antigens are those that have entered the body from outside through inhalation, ingestion or injection. Endogenous antigens are those that have been generated within previously-normal cells as a result of normal cell metabolism, or because of viral or intracellular bacterial infection. Auto antigens are those that are normal protein or protein complex present in the host body but can stimulate an immune response.

As used herein the term "epitope" or "immunoactive regions" refers to distinct molecular surface features of an antigen capable of being bound by component of the adaptive immune system, e.g., an antibody or T cell receptor. Antigenic molecules can present several surface features that can act as points of interaction for specific antibodies. Any such distinct molecular feature can constitute an epitope. Therefore, antigens have the potential to be bound by several distinct antibodies, each of which is specific to a particular epitope.

As used herein the term "antibody" or "immunoglobulin molecule" refers to a molecule naturally secreted by a particular type of cells of the immune system: B cells. There are five different, naturally occurring isotypes of antibodies, namely: IgA, IgM, IgG, IgD, and IgE.

As used herein the term "immune-related molecule" refers to a biological molecule involved in the activation or regulation of an immune response. These include, for example, an antibody, T cell receptor, or MHC complex (e.g., human leukocyte antigen).

As used herein, the term "inflammatory response molecule" refers to molecules that signal or mediate an inflammatory response, e.g., cytokines such as interleukin and tumor necrosis factor. Inflammatory response molecules include, for example, pro-inflammatory molecules.

As used herein, the term "autoimmune disorder" refers to any of a large group of diseases characterized by abnormal functioning of the immune system that causes a subject's immune system to damage the subject's own tissues. Celiac disorder, lupus erythematosis, and rheumatoid arthritis are examples of autoimmune disorders. Autoimmune disorders may be induced by environmental factors.

The term "percent identity" or "percent sequence identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website. Percent identity scores can be calculated using default values for this program as available on the National Center for Biotechnology Information website as of the priority date of this application.

As used herein the term "biologically active fragment" or variant thereof refers to a polypeptide capable of generating a substantially equal or greater T cell response in a subject sensitive to gluten as the polypeptide (e.g., GP or tTG) from which it is derived. In another embodiment, biologically active fragments are capable of generating at least 50%, more preferably at least 75% of the T cell response in a subject sensitive to gluten as the polypeptide from which it is derived. In an embodiment, biologically active fragments are 14, 13, 12, 11, 10, 9, 8 and no less than 7 amino acids in length. Deletions and/or additions at either end of any of the peptides are particularly contemplated. Examples of biologically active fragments disclosed herein include SEQ ID NO: 1-127.

The term "Celiac disease", also referred to herein as "CeD", refers to a chronic inflammatory disease of the small intestine. The disease encompasses a spectrum of conditions characterised by varying degrees of gluten sensitivity, including a severe form characterised by a flat small intestinal mucosa (hyperplastic villous atrophy) and other forms characterised by milder symptoms including fatigue, chronic diarrhea, malabsorption of nutrients, weight loss, abdominal distension, anemia as well as a substantially enhanced risk for the development of osteoporosis and intestinal malignancies (lymphoma and carcinoma).

The term "sensitive to gluten" refers to the state in which any one or more of the symptoms of Celiac disease or an inappropriate T cell response are exhibited by a subject exposed to gluten, or peptide fragment thereof. In a subject who is not sensitive to gluten, there is little or no T cell response caused by ingestion of gluten. By contrast, in a subject sensitive to gluten there is an inappropriate CD4$^+$ T cell mediated immune response to peptides derived from gluten after ingestion thereof.

The terms "immune tolerance", "immunological tolerance", "tolerance" or "desensitise" are here defined as to make a sensitised or hypersensitive subject, less sensitive, insensitive or nonreactive to gluten by reducing the immunological reactivity of a subject towards gluten. Immune tolerance may be generated, for example, by exposure of mucosal surfaces to tolerance-inducing antigenic fragments of gluten as defined herein. Mucosal administration of both high- and low-dose antigen may result in immune tolerance, in which the immune response to subsequent systemic administration of antigen is reduced. At least two mechanisms of immune tolerance may exist. Tolerance to high-doses of an antigen appears to occur by inactivation or clonal deletion of Th1 and Th2 cells. In contrast, tolerance to low doses of antigen leads to bystander immune suppression mediated by stimulation of Treg cells to produce suppressive cytokines such as interleukin-4 (IL-4), interleukin-10 (IL-10) and TGFβ.

The term "inducing immune tolerance" as used herein refers to bringing about, producing, or causing immune tolerance to gluten in a subject sensitive to gluten.

The term "hypersensitive" is here defined as abnormally susceptible physiologically to gluten.

The term "anergy" refers to a state of reversible unresponsiveness or hyporesponsiveness of a T cell (or B cell) to an antigen.

As used herein, "Treg" refers to a subclass of T cells whose major role is to bring T cell-mediated immunity during an immune reaction to an end, and to suppress auto-reactive T cells that escaped negative selection in the thymus. A "Treg response", as used herein, is characterised by the differentiation and proliferation of the population of CD4$^+$ or CD8$^+$ Treg cells which express the forkhead family transcription factor FOXP3 (forkhead box p3) and/or the MHC Class II associated protein LAG-3, and/or express high levels of the IL-2 receptor alpha chain (CD25). There is also a minor population of MHC Class I-restricted CD8$^+$ FOXP3-expressing Treg cells. The presence of Treg cells in the peripheral circulation or spleen may be determined by analysis of CD4$^+$/CD25$^+$ expression. This may conveniently be achieved using flow cytometry. In addition, Treg cells may be quantified by determining levels of FOXP3 mRNA in peripheral blood- or spleen-derived mononuclear cells by quantitative reverse transcriptase polymerase chain reaction (PCR). In addition, the induction of a Treg response in vivo may be assessed by the measurement of Treg-associated cytokines from peripheral blood- or lymph node-derived mononuclear lymphocytes. Treg cells typically show higher expression levels of the anti-inflammatory cytokines such as IL-10 and TGFβ and the presence of these mediators may be determined by methods known in the art, such as flow cytometry, immunohistochemical staining or ELISA.

The term "T cell stimulatory peptide" or "stimulatory peptide" refers to a peptide or epitope capable of activating a T cell.

The term "activate" or "activating" or "activation" in relation to a T cell refers to the presentation by an MHC molecule on one cell of an epitope to an appropriate T cell receptor on a second (T) cell, together with binding of a co-stimulatory molecule by the T cell, thereby eliciting a "T cell response".

As used herein, "toxic peptide" refers to a peptide that stimulates T cell activation in a subject.

The term "expansion" as used herein refers to the proliferation and amplification of a T cell population following T cell activation.

The term "immunodominant" refers to a subunit of a peptide (epitope) that is most easily recognized by the immune system and thus most influences the specificity of an induced immune response, such as a T cell response. "Immunodominant" may be used interchangeably with "dominant" herein.

As used herein, the term "modulating a T cell response" refers to regulating or adjusting a T cell response in a subject sensitive to gluten, such that the T cell response to gluten is reduced or lessened.

As used herein, "modifying cytokine secretion" refers to changing or altering somewhat the secretion of cytokines by a subject sensitive to gluten, such that the effects of gluten sensitivity in the subject are reduced or lessened. The term encompasses both increased secretion of a particular cytokine or combination of cytokines and decreased secretion of a particular cytokine or combination of cytokines.

As used herein, "epitope" refers to that portion of an antigen or a peptide that is recognized by the immune system, for example, a T cell receptor or the major histocompatibility complex (MHC) class I or class II, an antibody, a B cell receptor, which portion is sufficient for high affinity binding. Generally, a linear epitope for recognition will be at least about 3 amino acids in length, and may be 4, 5, 6, 7, 8, 9, 10, 11, 12, 13, 14, 15 amino acids in length, or more.

The term "polyepitope" refers to the presence of two or more epitopes (peptides) linked in a single polypeptide chain.

As used herein, "antigen" and "immunogen" and variations thereof are generally used interchangeably and refer to the epitope-containing structure recognized by the immune system.

The term "gluten" or "gluten protein" encompasses alpha (α), beta (β), gamma (γ) and omega (ω) gliadins, and low and high molecular weight (LMW and HMW) glutenins in wheat, B, C and D hordeins in barley, β, γ and ω secalins in rye, and optionally avenins in oats. "Gluten peptides" are peptides derived from, or encompassed within, one or more of the gluten proteins.

The term "gliadin", also referred to herein as "GP", refers to the aqueous alcohol-soluble fraction of gluten, particularly, but not exclusively, gluten derived from wheat, for example *Triticum aestivum*.

The term "glutenin" refers to the aqueous alcohol-insoluble fraction of gluten, particularly but not exclusively, gluten derived from wheat, for example *Triticum aestivum*.

As used herein, "hordein" or "barley hordein" refers to gluten derived from barley, Hordein *vulgare*.

As used herein, "secalin" or "rye secalin" refers to gluten derived from rye, *Secale* cerale.

As used herein, "avedin" or "oat avedin" refers to gluten derived from oats, *Avena sativa*. The terms "human leukocyte antigen" and "HLA" are here defined as a genetic fingerprint on human white blood cells and platelets, composed of proteins that play a critical role in activating the body's immune system to respond to foreign organisms. In humans and other animals, the HLA is also referred to as the "major histocompatibility complex" (MHC).

As used herein, "tissue transglutaminase", also referred to herein as "tTG", is a crucial factor in Celiac disease because it promotes gluten-specific T cell responses. tTG causes selective deamidation of gluten, which in turn, causes the generation of a series of gluten peptides that bind to HLA- DQ2 or -DQ8 molecules with high affinity. The resulting HLA-DQ2 (DQ8)-gluten peptide interaction triggers the proinflammatory CD4 T cell response. Thus, the term "deamidation" refers to the conversion of glutamine to glutamic acid, or to the conversion of asparagine to aspartic acid. As used herein, deamidation refers particularly to the conversion of glutamine to glutamic acid in gluten, a process that increases the propensity of gluten peptides to activate T cells.

As used herein, the term "agent" refers to a collection of peptides and/or polynucleotides. The peptides and/or poly-nucleotides may be in the same composition (such as a vaccine), in different compositions or a combination thereof (for example, the first and second peptide defined herein in one composition, and the third in a separate composition). If in different compositions, they will preferably be in close proximity, such as in a kit. Accordingly, the methods of the invention contemplate providing (for example administering to a subject) the individual component peptides and/or polynucleotides of an agent of the invention in a single composition (vaccine), or sequentially in different compositions or a combination thereof.

Before the disclosed embodiments are described in greater detail, it is to be understood that this disclosure is not limited to particular embodiments described, as such can, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the present disclosure. The upper and lower limits of these smaller ranges can independently be included in the smaller ranges and are also encompassed within the present disclosure, subject to any specifically excluded limit in the stated range. Where the stated range includes one or both of the limits, ranges excluding either or both of those included limits are also included in the present disclosure.

Certain ranges can be presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unre-cited number can be a number which, in the context in which it is presented, provides the substantial equivalent of the specifically recited number.

Unless defined otherwise, all technical and scientific terms used herein have the same meaning as commonly understood by one of ordinary skill in the art to which these disclosed embodiments belong. Although any methods and materials similar or equivalent to those described herein can also be used in the practice or testing of the disclosed embodiments, representative illustrative methods and mate-rials are now described. Any recited method can be carried out in the order of events recited or in any other order which is logically possible.

All publications and patents cited in this specification are herein incorporated by reference as if each individual pub-lication or patent were specifically and individually indi-cated to be incorporated by reference and are incorporated herein by reference to disclose and describe the methods and/or materials in connection with which the publications are cited.

It is noted that, as used herein and in the appended claims, the singular forms "a," "an," and "the" include plural referents unless the context clearly dictates otherwise.

Peptides

The present disclosure relates to the following peptides and modifications thereof. Some embodiments include novel and selective polyepitope-containing peptides that are agents or vaccines for treating and diagnosing CeD. In some embodiments, the polyepitope-containing peptides are anti-gens that modulate a T cell response of a subject who is sensitive to gluten or who has CeD. Examples of these polyepitope-containing and Celiac active peptides are pro-vided in Table 1.

TABLE 1

| tTG-DGP complex peptide sequences with immunogenic specificity for CeD | |
| --- | --- |
| SEQ ID NO: | Peptide Sequence |
| 1 | FEDGILEQPPEQ |
| 2 | PFPQKTVEIPEQ |
| 3 | FPLRDAPEQQPE |
| 4 | FPQQPFWLTEQP |
| 5 | FDVFAHPFPFPQ |
| 6 | AWCPADFPEEQP |
| 7 | FPEPAPSQEQPF |
| 8 | AEVSLQEQPPEQ |
| 9 | EMIWNFPFPEQP |
| 10 | EQPPEQAEVSLQ |
| 11 | FPEQPEYGDGVS |
| 12 | PFPPEQALLVEP |
| 13 | HDQNSNQPFQPE |
| 14 | PFPSVDILRQPE |
| 15 | EQPLTQQGFEQP |
| 16 | FPEFPEVVNFES |
| 17 | QPFQPEYNSAHD |
| 18 | DLCREKPEQEQP |
| 19 | EKLVVRPEQQPE |
| 20 | FPQPGYEGWEQP |
| 21 | QPEQPEYQGSSF |
| 22 | PFPNRSLIVQPF |
| 23 | DCTLSLPEQQPE |
| 24 | PFPSVDSLTFPE |
| 25 | DAVEEGQPEPEQ |
| 26 | ASTGYQQPEPFP |
| 27 | FEGRNYFPEFPQ |

TABLE 1-continued

| tTG-DGP complex peptide sequences with immunogenic specificity for CeD | |
|---|---|
| SEQ ID NO: | Peptide Sequence |
| 28 | EQPLQNPLPQPF |
| 29 | GWQALDFPQPFP |
| 30 | PEQRKLVAEFPE |
| 31 | QPEPVPVRAFPQ |
| 32 | PFPQPFVFAEVN |
| 33 | QPFLAERDLFPE |
| 34 | PEQPEQVDQQDC |
| 35 | EQPSGMVNCEQP |
| 36 | FPELCARTVPFP |
| 37 | PFPLLFNAWPFP |
| 38 | HLNKLAPEQQPE |
| 39 | EQPNAPIGLPFP |
| 40 | FPEREAFTREQP |
| 41 | FPQPFPAAVACT |
| 42 | QPFPEQYCCGPV |
| 43 | EQPQSMNMGPFP |
| 44 | CRLLLCPEQPEQ |
| 45 | IPTRVVFPEEQP |
| 46 | QPFLHMGLHQPE |
| 47 | PFPLSLEASQPE |
| 48 | FPQNGRDHHQPF |
| 49 | QPENNTAEEFPE |
| 50 | PFPLDPTPQQPF |
| 51 | AHITNNEQPEQP |
| 52 | FPQKVRMDLQPF |
| 53 | FPEMGSDFDQPF |
| 54 | PEQKSVGRDQPE |
| 55 | IKVRALPFPPEQ |
| 56 | FPENFHCWVPEQ |
| 57 | GRVVSGFPQQPF |
| 58 | QPEPFPASTGYQ |
| 59 | AAVACTFPQPFP |
| 60 | PFPPEQWMTRPD |
| 61 | PEQEQPWVESWM |
| 62 | QPEPVYVGRFPE |
| 63 | PEQNYEASVQPF |
| 64 | EQPQPFVVDWIQ |
| 65 | QPEQPEYPEGSS |

TABLE 1-continued

| tTG-DGP complex peptide sequences with immunogenic specificity for CeD | |
|---|---|
| SEQ ID NO: | Peptide Sequence |
| 66 | PFPPKQKRKQPF |
| 67 | QPFNFGQFEEQP |
| 68 | QPEQPFVNADVV |
| 69 | ALLVEPPFPPEQ |
| 70 | EGDLSTQPFQPF |
| 71 | PEQNCNDDQQPF |
| 72 | PFPTRANHLPEQ |
| 73 | DQGVLLPEQQPE |
| 74 | GPECGTFPQQPF |
| 75 | FPQLVLERCQPF |
| 76 | QPFEQPVVTNYN |
| 77 | GLYRLSQPFEQP |
| 78 | ADAVYLPEQQPF |
| 79 | FPQSEGTYCQPE |
| 80 | FPQSNLLIEPEQ |
| 81 | ENPEIKFPQPFP |
| 82 | QPFQEYVLTFPQ |
| 83 | QPFSWIGSVFPQ |
| 84 | EDITHTEQPQPF |
| 85 | CQRVKYQPEPEQ |
| 86 | EIPDPVFPQQPE |
| 87 | EGAGLTQPEPEQ |
| 88 | QPESFVLGHPEQ |
| 89 | PEQKNHGCQEQP |
| 90 | PFPPQEKSEEQP |
| 91 | QPFPVEAGEFPE |
| 92 | EQPMAEELVFPE |
| 93 | IKIRILPFPPEQ |
| 94 | ILDICLPFPFPQ |
| 95 | FPELTLHFEFPE |
| 96 | DLYLENQPFPEQ |
| 97 | HTYKYPPFPFPQ |
| 98 | EQPFPEVIIGPA |
| 99 | DGSVHKFPEPFP |
| 100 | FPQLEGCTFFPE |
| 101 | QPERCDLELQPF |
| 102 | QPETKARFPQPE |

TABLE 1-continued

| tTG-DGP complex peptide sequences with immunogenic specificity for CeD | |
| --- | --- |
| SEQ ID NO: | Peptide Sequence |
| 103 | FPQRNEFGEFPE |
| 104 | CWVFAAFPQQPE |
| 105 | FPELAEKEEQPE |
| 106 | QPFPFPWDNNYG |
| 107 | FPQRRSSPVFPE |
| 108 | ESNLIKPEQQPF |
| 109 | DLLPLHEQPFPE |
| 110 | DCLTESQPFPEQ |
| 111 | GHFILLPEQQPE |
| 112 | FSEKSVFPEQPE |
| 113 | QPEEQPTVSYNG |
| 114 | GEEVKVPEQPEQ |
| 115 | EPVINSQPEPEQ |
| 116 | EEERQEEQPQPF |
| 117 | HHTADLQPEQPE |
| 118 | GTKYLLPFPFPE |
| 119 | EQPTFTVEGPFP |
| 120 | GEIQGDQPEQPF |
| 121 | PFPLPVALEFPE |
| 122 | CILYEKEQPFPE |
| 123 | QPFPKFLKNQPE |
| 124 | FPQLTFSVVPEQ |
| 125 | PFPEQPVVTGPA |
| 126 | EKYRDCFPEPEQ |
| 127 | PFPTATVVDQPE |
| 128 | PFPLDVNPKQPF |
| 129 | FPQQGSAKFQPE |
| 130 | PFPRDEREDQPF |
| 131 | EQPEQPVRRGQP |
| 132 | PFPSVPLCIQPE |
| 133 | ILGEPKQPFQPE |
| 134 | FPQPFPVSPMSW |
| 135 | QPELHKLVVQPE |
| 136 | GFIYQGFPQPFP |
| 137 | EQPEQPAHITNN |
| 138 | EEYVCRFPEPFP |
| 139 | PEQPDLQPGQPE |
| 140 | QPFFPQTTPANA |

TABLE 1-continued

| tTG-DGP complex peptide sequences with immunogenic specificity for CeD | |
| --- | --- |
| SEQ ID NO: | Peptide Sequence |
| 141 | EQPLTEEQKQPE |
| 142 | ESDKLKQPFPEQ |
| 143 | EQPNGILGPEQP |
| 144 | PFPQEAGTKFPQ |
| 145 | EETGMAPFPEQP |
| 146 | PFPMAMRIRQPF |
| 147 | QPELLGRWDQPE |
| 148 | DAPFVFQPFQPF |
| 149 | IEYFRNEQPFPE |
| 150 | QPESTKYDAQPF |
| 151 | CLILLDQPEPFP |
| 152 | FPERCLGIPEQP |
| 153 | EQPNIPWNFPFP |
| 154 | GDKSEMPEQFPE |
| 155 | PFPFPQYLDSEE |
| 156 | FPENSYLLAPEQ |
| 157 | EQPRAIKEGQPF |
| 158 | CTVLRCFPQEQP |
| 159 | PEQKYGQCWFPQ |
| 160 | EGDWTAPEQEQP |
| 161 | PEQQPFADAVYL |
| 162 | PFPLKAVKGEQP |
| 163 | EQPSSEEREPFP |
| 164 | EQPRDCSRRPEQ |
| 165 | EQPNVIIGPFPE |
| 166 | PEQLLNLNLPEQ |
| 167 | EQPSLQLTTFPE |
| 168 | PEQNLEPFSQPF |
| 169 | HKSINRFPEEQP |
| 170 | EQPLRRWKNPEQ |
| 171 | PFPKNAGRDEQP |
| 172 | ELETNGPFPQPF |

Disclosed herein are methods of identifying novel poly-epitope-containing peptides and the use of those novel polyepitope-containing peptides. The novel polyepitope-containing peptides can comprise epitope sequences of proteins that stimulate antibody production in subjects having an autoimmune disease, and epitope sequences of bioactive polypeptides that generate an immune response in subjects having an autoimmune disease. The proteins that stimulate antibody production in subjects having an auto-immune disease can comprise self-antigens. For example, the proteins can include tTG. In embodiments in which the autoimmune disease is CeD, the bioactive polypeptides that generate an immune response can include GPs, such as alpha gliadin, beta gliadin, gamma gliadin, or omega gliadin, or another wheat-related proteins or peptides. In further embodiments, the bioactive polypeptides that generate an immune response can include DGPs. Therefore, in certain embodiments, the novel polyepitope-containing peptides can include epitopes of a tTG-DGP complex. Uses of the arrays or formulations comprising the novel polyepitope-containing peptides disclosed herein can include research applications, therapeutic purposes, medical diagnostics, and/or stratifying one or more patients or subjects.

The novel polyepitope-containing peptides and/or its components can also include biologically active variants. Biologically active variants include peptides which vary by one or more amino acids from the defined peptide, which are also known in the art as homologues. For example, a variant can comprise one or more amino acid substitutions in any one or more of the peptides. As used herein, "substituted" or "substitution" includes substitution, replacement, addition, insertion, omission and/or deletion (as such variants may also be fragments) of an amino acid residue(s). In particular, this refers to peptides having conservative substitution without losing, or significantly diminishing, their use in the methods of the invention. Preferably, biologically active variants are capable of generating a substantially equal or greater T cell response in a subject sensitive to gluten as the peptide from which it is derived. In another embodiment, biologically active variants are capable of generating at least 50%, more preferably at least 75% of the T cell response in a subject sensitive to gluten as the peptide from which it is derived.

Biologically active variants of the peptides may be identified by modifying the sequence of each peptide and then assaying the resulting peptide for the ability to stimulate an immune response, for example, production of T cells.

In an embodiment, no more than 5, more preferably no more than 4, more preferably no more than 3, more preferably no more than 2, and even more preferably only 1 amino acid in a defined peptide is varied (by substitution, deletion or addition), when compared to a peptide sequence defined herein.

In an alternate embodiment, the percentage identity between a particular sequence (variant) and a reference sequence (peptide defined herein) is at least about 60% or at least about 70% or at least about 80% or at least about 90% or at least about 95% or above such as at least about 96%, 97%, 98%, 99% or greater. Percentage identity can be determined using readily available software packages, such as BLAST (www.ncbi.nlm.nih.gov/) and GAP.Natural amino acids include alanine (A), arginine (R), asparagine (N), aspartic acid (D), cysteine (C), glutamine (Q), glutamic acid (E), glycine (G), histidine (H), isoleucine (I), leucine (L), lysine (K), methionine (M), phenylalanine (F), proline (P), serine (S), threonine (T), tryptophan (W), tyrosine (Y), valine (V), hydroxyproline (O and/or Hyp), isodityrosine (IDT), and di-isodityrosine (di-IDT). Hydroxyproline, isodi-tyrosine, and di-isodityrosine are formed post-translation-ally. Use of natural amino acids, in particular the 20 geneti-cally encoded amino acids, is particularly contemplated.

Substitutions may be conservative amino acid substitu-tions, in which the substituted amino acid has similar structural or chemical properties with the corresponding amino acid in the reference sequence. Alternatively, the substitutions may be non-conservative amino acid substitu-tions as long as the desired activity is maintained.

By way of example, conservative amino acid substitutions involve substitution of one aliphatic or hydrophobic amino acids, for example, alanine, valine, leucine and isoleucine, with another; substitution of one hydroxyl-containing amino acid, for example, serine and threonine, with another; sub-stitution of one acidic residue, for example, glutamic acid or aspartic acid, with another; replacement of one amide-containing residue, for example, asparagine and glutamine, with another; replacement of one aromatic residue, for example, phenylalanine and tyrosine, with another; replace-ment of one basic residue, for example, lysine, arginine and histidine, with another; and replacement of one small amino acid, for example, alanine, serine, threonine, methionine, and glycine, with another.

Peptide variants may be produced by mutagenesis or other chemical methods. Alanine scanning is a useful technique for identifying important amino acids. In this technique, an amino acid residue is replaced by Ala and its effect on the peptide's activity is determined. For example, cysteine resi-dues may be substituted to minimize dimerization via dis-ulfide linkages. Each of the amino acid residues of the peptide is analyzed in this manner to determine the impor-tant regions of the peptide. Means for preparing such pep-tides are well understood in the art.

In addition to naturally occurring amino acids, non-naturally occurring amino acids, or modified amino acids, are also contemplated and within the scope of the invention. In fact, as used herein, "amino acid" refers to naturally occurring amino acids, non-naturally occurring amino acids, and amino acid analogues, and to the D or L stereoisomers of each.

The phrases "protecting group" and "blocking group" as used herein, refers to modifications to the peptide which protect it from undesirable chemical reactions, particularly in vivo. Examples of such protecting groups include esters of carboxylic acids and boronic acids, ethers of alcohols and acetals, and ketals of aldehydes and ketones. Examples of suitable groups include acyl protecting groups such as, for example, furoyl, formyl, adipyl, azelayl, suberyl, dansyl, acetyl, theyl, benzoyl, trifluoroacetyl, succinyl and methox-ysuccinyl; aromatic urethane protecting groups such as, for example, benzyloxycarbonyl (Cbz); aliphatic urethane pro-tecting groups such as, for example, t-butoxycarbonyl (Boc) or 9-fluorenylmethoxy-carbonyl (FMOC); pyroglutamate and amidation. Many other modifications providing increased potency, prolonged activity, ease of purification, and/or increased half-life will be known to the person skilled in the art.

In one embodiment, one of more glutamate residues of one or more of the peptides may be generated by tTG activity upon a peptide. In alternate embodiment, this reac-tion occurs in vivo following administration.

The peptides may comprise one or more modifications, which may be natural post-translation modifications or arti-ficial modifications. The modification may provide a chemi-cal moiety (typically by substitution of a hydrogen, for example, of a C—H bond), such as an amino, acetyl, acyl, carboxy, hydroxy or halogen (for example, fluorine) group, or a carbohydrate group. Typically, the modification is present on the N- or C-terminal. Furthermore, one or more of the peptides may be PEGylated, where the PEG (poly-ethyleneoxy group) provides for enhanced lifetime in the blood stream. One or more of the peptides may also be combined as a fusion or chimeric protein with other proteins, or with specific binding agents that allow targeting to specific moieties on a target cell.

Peptide variants may be obtained in which the peptide has been chemically modified at the level of amino acid side chains, of amino acid chirality, and/or of the peptide backbone Certain peptides described herein may exist in particular geometric or stereoisomeric forms. The present invention contemplates all such forms, including cis-(Z) and trans-(E) isomers, R- and S-enantiomers, diastereomers, (D)-isomers, (L)-isomers, the racemic mixtures thereof, and other mixtures thereof, as, falling within the scope of the invention. Additional asymmetric carbon atoms may be present in a substituent, such as an alkyl group. All such isomers, as well as mixtures thereof, are intended to be included in this invention.

In another example, to prevent cleavage by peptidases, any one or more of the peptides may include a non-cleavable peptide bond in place of a particularly sensitive peptide bond to provide a more stable peptide. Such non cleavable peptide bonds may include beta amino acids.

In certain embodiments, any one or more of the peptides may include a functional group, for example, in place of the scissile peptide bond, which facilitates inhibition of a serine-, cysteine- or aspartate-type protease, as appropriate. For example, the invention includes a peptidyl diketone or a peptidyl keto ester, a peptide haloalkylketone, a peptide sulfonyl fluoride, a peptidyl boronate, a peptide epoxide, a peptidyl diazomethane, a peptidyl phosphonate, isocoumarins, benzoxazin-4-ones, carbamates, isocyantes, isatoic anhydrides or the like. Such functional groups have been provided in other peptide molecules, and general routes for their synthesis are known.

A variant may be a mimetic. The term "mimetic" is intended to refer to a substance which has some chemical similarity to the molecule it mimics and retains a particular activity of interest (for example, inducing tolerance). The underlying rationale behind the use of peptide mimetics, is that the peptide backbone of proteins exists chiefly to orient amino acid side chains in such a way as to facilitate molecular interactions, such as those of T cell and MHC-peptide, antibody and antigen, enzyme and substrate or scaffolding proteins. A peptide mimetic is designed to permit molecular interactions similar to the natural molecule. Mimetics include olefins, phosphonates, aza-amino acid analogues and the like. Persons skilled in the art would readily appreciate methods for designing mimetics of peptides and would be able to utilize them to design mimetics of the peptides defined herein.

The peptides may be analyzed by hydrophilicity analysis, which can be used to identify the hydrophobic and hydrophilic regions of the peptide, thus aiding in the design of peptides for experimental manipulation, such as in binding experiments, antibody synthesis, etc. Secondary structural analysis may also be performed to identify regions of a peptide that adopt specific structural motifs. Manipulation, translation, secondary structure prediction, hydrophilicity and hydrophobicity profiles, open reading frame prediction and plotting, and determination of sequence homologies, can be accomplished using computer software programs available in the art. Other methods of structural analysis including, but not limited to, X-ray crystallography, mass spectrometry and gas chromatography, computer modelling, optical rotary dispersion (ORD), or circular dichroism (CD) may also be used.

The peptides, fragments or variants may be in a salt form, preferably, a pharmaceutically acceptable salt form. "A pharmaceutically acceptable salt form" includes the conventional non-toxic salts or quaternary ammonium salts of a peptide, for example, from non-toxic organic or inorganic acids. Conventional non-toxic salts include, for example, those derived from inorganic acids such as hydrochloride, hydrobromic, sulphuric, sulfonic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

The peptides can be provided in the agent or vaccine as separate peptides or linked, for example, in a polyepitope structure. In one embodiment, the peptides may be presented in a single polypeptide chain (polyepitope string), i.e., in a linear or circular arrangement. In another embodiment, the peptides can be presented in a multiple antigen presentation system, particularly based on a dendrimer backbone such as polylysine. A polylysine backbone provides a non-linear, branched arrangement of epitopes. This system provides the advantage over a polyepitope string that the peptides do not interfere with each other or be liable to cleavage into cryptic epitopes and thus are able to induce a full T cell response.

Conjugates

One or more of the peptides may be conjugated to a compound using standard methods. Examples of compounds to which the peptides can be conjugated include but are not limited to a radioisotope, a fluorescent label, a chemiluminescent compound, an enzyme label, a free radical, an avidin-biotin label, a bacteriophage label, a compound that increases the half life of the peptide in a subject, an adjuvant, an MHC molecule or fragment thereof.

The compound may facilitate detection and/or isolation or increase immunogenicity of the conjugated peptide.

"Conjugated" as used herein means coupled via covalent or non-covalent bonds. While covalent bonds are preferred, the compound may also be linked to the peptide via complexation without covalent linkage, for example, via hydrogen bonds or electrostatic, hydrophobic, etc., interaction.

Typical radioactive isotopes include $^3H$, $^{125}I$, $^{131}I$, $^{32}P$, $^{35}S$, $^{14}C$, $^{51}Cr$, $^{36}Cl$, $^{57}Co$, $^{58}Co$, $^{59}Fe$, $^{75}Se$, and 152 Eu.

Typical fluorescent labels include fluorescein isothiocyanate, rhodamine, phycoerythrin, phycocyanin, allophycocyanin, o-phthaldehyde, and fluorescamine.

Typical chemiluminescent compounds include luminol, isoluminol, aromatic acridinium esters, imidazoles, acridinium salts, and the oxalate esters. Typical bioluminescent compounds include luciferin, luciferase, and aequorin.

Typical enzyme labels include alkaline phosphatase, beta-galactosidase, glucose-6-phosphate dehydrogenase, maleate dehydrogenase, glucose oxidase, and peroxidase.

In one embodiment, a non-specific linker is included between the compound and the peptide to which it is conjugated. Such a linker is not involved in peptide activity. Rather the linker may serve as a spacer between the peptide and a functional moiety. Uses for a linker include immobilization of the peptide, such as to aid purification or detection. Alternatively, a linker may allow attachment of a compound to the peptide that enables specific delivery of the peptide to a particular target, such as a cell or tissue, spatially or temporally. When used as a vaccine, one or more of the peptides may be coupled to a linker that serves as a spacer between the peptide and an immunogenic carrier, or permits improved coupling between the peptide and the immunogenic carrier and prevents the formation of cryptic epitopes.

In one embodiment, one or more of the peptides are covalently coupled to an adjuvant (immunogenic carrier protein), such as diphtheria toxoid (DT), keyhole limpet hemocyanin (KLH), tetanus toxoid (TT) or the nuclear protein of influenza virus (NP), to increase their immunogenicity, using any of several conjugation chemistries known in the art. A non-specific linker can be present between the peptide and the immunogenic carrier and is preferably joined to the peptide or co-synthesized to facilitate coupling to the immunogenic carrier and/or to serve as a spacer between the peptide and the immunogenic carrier.

When used as a diagnostic agent, one or more of the peptides are preferably conjugated to an immunogenic carrier that was not previously used for vaccination. When monitoring the success of vaccination, this prevents the diagnostic agent from reacting to antibodies that were formed against the carrier fraction of the vaccine.

In one embodiment, the compound is an MHC class II molecule or peptide binding fragment thereof. The MHC class II molecule may be purified from a biological sample. Alternatively, the MHC class II molecule may be recombinantly produced. A peptide binding fragment of the MHC class II molecule can be obtained, for example, by enzymatic cleavage of the purified or recombinant intact molecule. Alternatively, the peptide binding fragment may be recombinantly produced. In a preferred embodiment, the compound is a recombinant two domain MHC class II molecule.

In their most basic form, the two domain MHC class II molecule comprises the al and $\beta 1$ domain of a mammalian MHC class II molecule wherein the amino terminus of the al domain is covalently linked to the carboxy terminus of the $\beta 1$ domain and wherein the polypeptide does not include the $\alpha 2$ or $\beta 2$ domains. The two domain MHC class II molecule is associated by covalent or non-covalent interaction with a peptide defined herein. In certain embodiments, the peptide is covalently linked to the amino terminus of the $\beta 1$ domain of the class II molecule. The two domain MHC class II molecule may also comprise a detectable label, such as a fluorescent label, or a toxin. Where the detectable label or toxin is to be covalently linked to the MHC molecule in a directed manner (i.e., rather than being randomly attached) it will generally be linked to the carboxy terminus of the molecule so as to minimize interference with the peptide antigen linked at the amino terminus.

In vitro, the two domain MHC class II molecule may be used to detect and quantify T-cells, and regulate T-cell function. Thus, such molecules loaded with a selected peptide may be used to detect, monitor and quantify the population of T cells that are specific for that peptide. The two domain MHC class II molecule/peptide conjugate may also be used to induce anergy of gluten-specific T-cells, alleviating symptoms associated with CeD. Alternatively, such molecules may be conjugated with a toxin to more directly kill the disease-causing T cells. Suitable toxins include protein toxins (for example, ricin, diphtheria, and *Pseudomonas* toxin), chemotherapeutic agents (for example, doxorubicin, daunorubicin, methotrexate, cytotoxin, and antisense RNA), antibodies to a cytotoxic T-cell surface molecule, lipases, and radioisotopes emitting "hard", for example, beta radiation.

Antigen Presenting Cells

The agent and/or peptides defined herein may be delivered by loading APCs with, for example, the first, second and third peptides, a biologically active fragment or variant of one or more thereof, and/or a polynucleotide encoding one or more thereof.

Preferably, the APCs are selected from the group consisting of dendritic cells, macrophages, B-lymphocytes and liver sinusoidal endothelial cells that express MHC class II molecules shared with the MHC phenotype of the subject. For example, the APCs may express HLA-DQ2 (for example, HLA DQA1*05 and HLA DQB1*02) and/or HLA DQ8. The APCs employed for this purpose may be isolated from the subject to whom they are to be delivered after loading, or they may be obtained from an allo-matched subject.

By "loading" an APC it is meant that the APC is incubated or transfected with the peptides, a biologically active fragment or variant of one or more thereof, or a polynucleotide encoding one or more thereof. Loading an APC can be achieved by using conventional nucleic acid transfection methods, such as lipid-mediated transfection, electroporation, and calcium phosphate transfection.

Peptide Production

The peptides can be prepared in any suitable manner. For example, the peptides can be recombinantly and/or synthetically produced.

The peptides may be synthesized by standard chemistry techniques, including synthesis by automated procedure using a commercially available peptide synthesizer. In general, peptide analogues are prepared by solid-phase peptide synthesis methodology which may involve coupling each protected amino acid residue to a resin support, preferably a 4-methylbenzhydrylamine resin, by activation with dicyclohexylcarbodiimide to yield a peptide with a C-terminal amide. Alternatively, a chloromethyl resin (Merrifield resin) may be used to yield a peptide with a free carboxylic acid at the C-terminal. After the last residue has been attached, the protected peptide-resin is treated with hydrogen fluoride to cleave the peptide from the resin, as well as deprotect the side chain functional groups. Crude product can be further purified by gel filtration, high pressure liquid chromatography (HPLC), partition chromatography, or ion-exchange chromatography.

If desired, and as outlined above, various groups may be introduced into the peptide of the agent during synthesis or during expression, which allow for linking to other molecules or to a surface. For example, cysteines can be used to make thioethers, histidines for linking to a metal ion complex, carboxyl groups for forming amides or esters, amino groups for forming amides, and the like.

The peptides may also be produced using cell-free translation systems. Standard translation systems, such as reticulocyte lysates and wheat germ extracts, use RNA as a template; whereas "coupled" and "linked" systems start with DNA templates, which are transcribed into RNA then translated.

Alternatively, the peptides may be produced by transfecting host cells with expression vectors that comprise a polynucleotide(s) that encodes one or more peptides.

For recombinant production, a recombinant construct comprising a sequence which encodes one or more of the peptides is introduced into host cells by conventional methods such as calcium phosphate transfection, DEAE-dextran mediated transfection, microinjection, cationic lipid-mediated transfection, electroporation, transduction, scrape lading, ballistic introduction or infection.

One or more of the peptides may be expressed in suitable host cells, such as, for example, mammalian cells (for example, COS, CHO, BHK, 293 HEK, VERO, HeLa, HepG2, MDCK, W138, or NIH 3T3 cells), yeast (for example, *Saccharomyces* or *Pichia*), bacteria (for example, *E. coli, P. pastoris,* or *B. subtilis*), insect cells (for example, baculovirus in Sf9 cells) or other cells under the control of appropriate promoters using conventional techniques. Following transformation of the suitable host strain and growth of the host strain to an appropriate cell density, the cells are harvested by centrifugation, disrupted by physical or chemical means, and the resulting crude extract retained for further purification of the peptide or variant thereof.

Suitable expression vectors include, for example, chromosomal, non-chromosomal and synthetic polynucleotides, for example, derivatives of SV40, bacterial plasmids, phage DNAs, yeast plasmids, vectors derived from combinations of plasmids and phage DNAs, viral DNA such as vaccinia viruses, adenovirus, adeno-associated virus, lentivirus, canary pox virus, fowl pox virus, pseudorabies, baculovirus, herpes virus and retrovirus. The polynucleotide may be introduced into the expression vector by conventional procedures known in the art.

The polynucleotide which encodes one or more peptides may be operatively linked to an expression control sequence, i.e., a promoter, which directs mRNA synthesis. Representative examples of such promoters include the LTR or SV40 promoter, the *E. coli* lac or trp, the phage lambda PL promoter and other promoters known to control expression of genes in prokaryotic or eukaryotic cells or in viruses. The expression vector may also contain a ribosome binding site for translation initiation and a transcription terminator.

The expression vectors may also include an origin of replication and a selectable marker, such as the ampicillin resistance gene of *E. coli* to permit selection of transformed cells, i.e., cells that are expressing the heterologous polynucleotide. The nucleic acid molecule encoding one or more of the peptides may be incorporated into the vector in frame with translation initiation and termination sequences.

One or more of the peptides can be recovered and purified from recombinant cell cultures (i.e., from the cells or culture medium) by well known methods including ammonium sulphate or ethanol precipitation, acid extraction, anion or cation exchange chromatography, phosphocellulose chromatography, hydrophobic interaction chromatography, affinity chromatography, hydroxyapatite chromatography, lectin chromatography, and HPLC. Well known techniques for refolding proteins may be employed to regenerate active conformation when the peptide is denatured during isolation and or purification.

To produce a glycosylated peptide, it is preferred that recombinant techniques be used. To produce a glycosylated peptide, it is preferred that mammalian cells such as, COS-7 and Hep-G2 cells be employed in the recombinant techniques.

The peptides can also be prepared by cleavage of longer peptides, especially from food extracts.

Pharmaceutically acceptable salts of the peptides can be synthesized from the peptides which contain a basic or acid moiety by conventional chemical methods. Generally, the salts are prepared by reacting the free base or acid with stoichiometric amounts or with an excess of the desired salt-forming inorganic or organic acid or base in a suitable solvent.

Methods of Identifying Peptide Sequences

Disclosed herein are novel, synthetic polyepitope-containing peptide sequences generated by novel methods of discovery and generation. Also disclosed herein are novel epitope sequences generated by novel methods of epitope discovery and generation. In one embodiment, a method of generating novel, synthetic peptide sequences involves discovery of novel epitope sequences on polypeptides capable of binding to antibodies or eliciting an immune response in subjects having an autoimmune disease and on polypeptides that stimulate antibody production in subjects having an autoimmune disease. Once epitope sequences are discovered, they are recombined with other discovered epitope sequences or with random sequences to generate new synthetic polypeptide sequences with greater sensitivity and specificity for binding to antibodies associated with an autoimmune disorder than the native epitopes alone. In preferred embodiments, the process of generating and screening sequences is performed on a peptide array that is configured to contact a sample.

Figure 1:
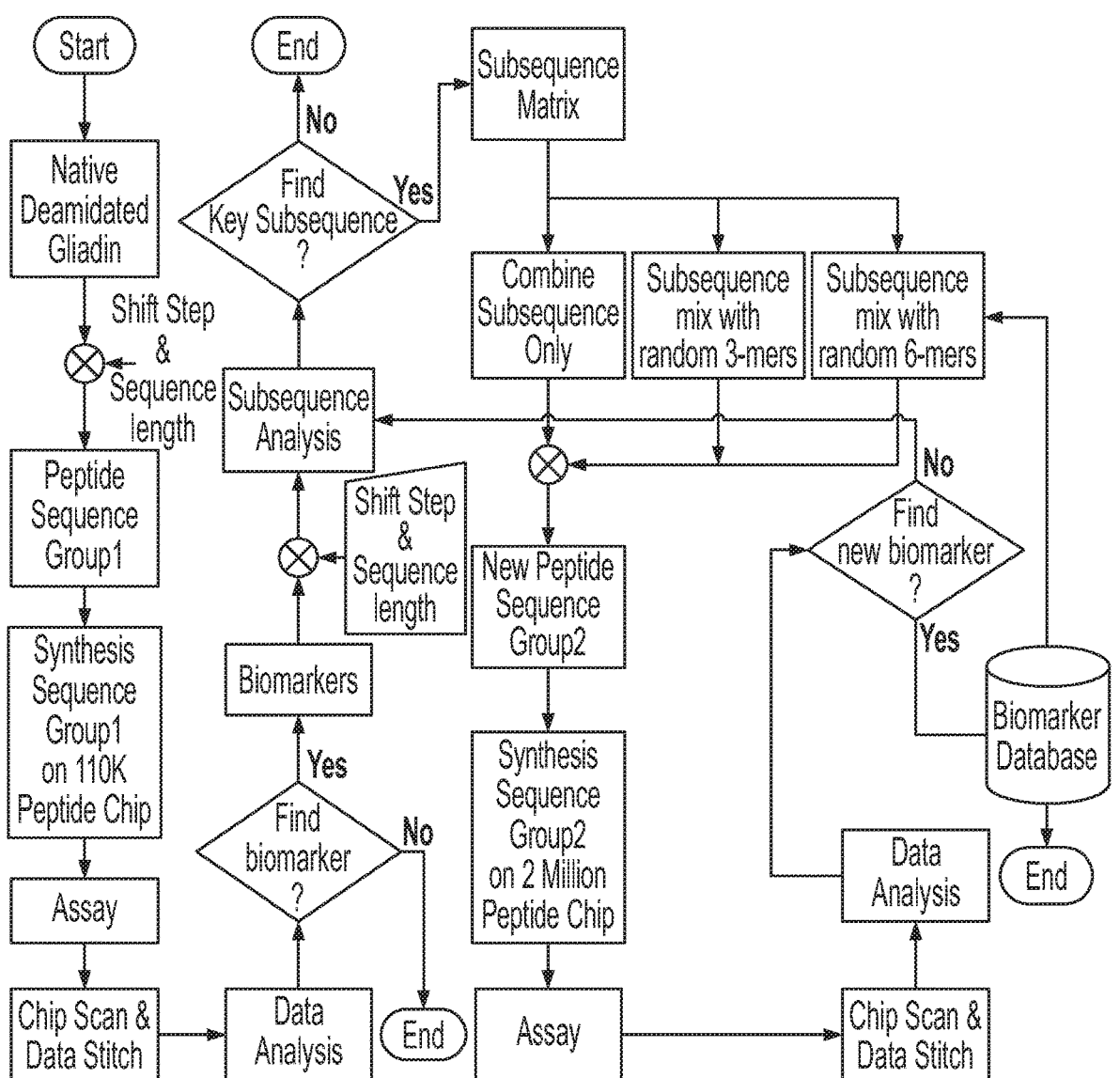
FIG. 1 is a flow chart for biomarker selection, training set analysis, and validation set analysis, in accordance with an embodiment.

In some embodiments, as illustrated in FIG. 1, the method of identifying novel epitopes comprises the steps of: 1) generating a first plurality of overlapping polypeptide fragments each comprising a portion of a native active protein or polypeptide; 2) determining specificity and sensitivity of antibodies correlated with an autoimmune disorder to each polypeptide fragment by contacting an array comprising the polypeptide fragments with a sample from a subject having the autoimmune disorder; 3) selecting polypeptide fragments that exceed a pre-defined threshold value for sensitivity and/or specificity of binding, or have the greatest values of sensitivity and/or specificity of the collection of polypeptide fragments; 4) identifying from the polypeptide fragments identified in Step 3 the occurrence of epitope sequences within the polypeptide fragments; 5) generating a second plurality of synthetic polypeptides each comprising at least two of the epitope sequences in step 4, and optionally containing at least one random polypeptide sequence; 6) determining the specificity and sensitivity for each of the synthetic polypeptides generated in step 5 by contacting an array comprising the synthetic polypeptide fragments with a sample from a subject having the immune disorder; and 7) selecting synthetic polypeptides from step 6 exceeding a specificity and sensitivity threshold to use as biomarkers for the autoimmune disorder. Optionally, steps 5 through 7 may be repeated to further refine the sensitivity and/or specificity of the synthetic polypeptides to binding of an antibody associated with an autoimmune disorder. This method results in the generation of a plurality of novel synthetic polypeptides useful for diagnosis and treatment of an autoimmune disorder (e.g., CeD).

In one embodiment, the autoimmune disorder is CeD. In one embodiment, the proteins from which the novel synthetic polypeptides are created are GPs and tTGs. In one embodiment, the GP is an α-gliadin, β-gliadin, γ-gliadin, or ω-gliadin.

Identification of Epitopes of an Antigen

Figure 2A:
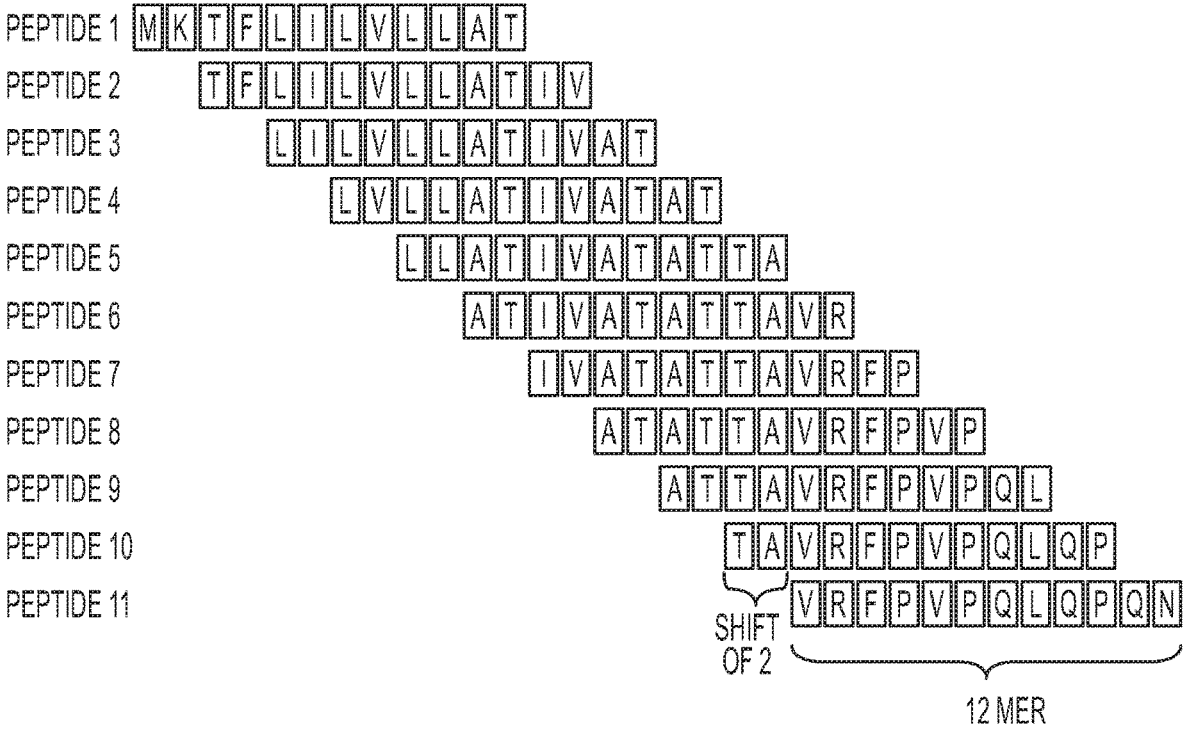
FIG. 2A is a proposed scheme for peptide synthesis on an array, in accordance with an embodiment.

As disclosed herein, methods of identifying epitopes of proteins, such as GP and tTG, are provided and used for generation of novel, synthetic polypeptide sequences for use in diagnosis and treatment of an autoimmune disease. In one embodiment, a full length polypeptide sequence is divided into overlapping polypeptide fragments of a discrete length. In one embodiment, each polypeptide fragment is from 6 to 15 amino acids in length. In one embodiment, each polypeptide fragment is 6, 7, 8, 9, 10, 11, 12, 13, 14, or 15 amino acids in length. In a preferred embodiment, each polypeptide fragment is 12 amino acids in length. The amount of overlap between polypeptide fragments of the full length polypeptide can be determined by step size between the polypeptide fragments, indicating the distance between each N-terminal or C-terminal amino acid of each polypeptide fragment as determined by the full length polypeptide. A diagram of an embodiment with a step size of 2 amino acids is shown in FIG. 2A with a polypeptide fragment length of 12 amino acids. This results in an overlap of 10 amino acids between neighboring polypeptide fragments. The overlap allows more precise determination of active epitope sequences on the polypeptide sequence. In some embodiments, the step size may vary, e.g., the step size may be 1, 2, 3, 4, 5, 6, 7, 8, 9, 10, 11, or 12 amino acids. In a preferred embodiment, the step size is 2 amino acids. One amino acid step size may also be used to improve precision at the cost of requiring generation of more fragment polypeptides.

Based upon the scheme of generation of polypeptide fragments discussed above, fragment polypeptides are synthesized on an array for screening against a sample with antibodies correlated with an autoimmune disorder. Binding of antibodies to fragment polypeptides on the array is detected via secondary antibody, although other methods of detection known to one of skill in the art will also suffice. Information about the binding of each polypeptide fragment to an antibody in a samples from a subject identified as having or not having the autoimmune disorder are compared to determine sensitivity and specificity of each peptide. Overlapping regions allow identification of epitope sequences. In one embodiment, the identified epitopes are from 3 to 11 amino acids in length. In one embodiment, each identified epitope is 3, 4, 5, 6, 7, 8, 9, 10, or 11 amino acids in length. In one preferred embodiment, each epitope is limited to 3 amino acids in length.

In some embodiments, for example in embodiments in which the polypeptide comprises a bioactive polypeptide such as a GP, epitope pairs are identified in polypeptide fragments above a threshold of specificity and/or sensitivity of binding to autoimmune-positive samples. These epitope pairs can then be used to generate novel bioactive sequences as described below.

Generation of Novel Bioactive Sequences

Using the epitopes identified from the native bioactive polypeptides described above, novel synthetic bioactive polypeptide sequences are generated and synthesized on an array for further screening. In one embodiment, each novel synthetic bioactive polypeptide comprises at least one epitope identified by the methods disclosed herein. In another embodiment, each novel synthetic bioactive polypeptide comprises at least two epitopes identified by the methods disclosed herein. In some embodiments, each novel synthetic bioactive polypeptide comprise two, three, four, or five epitopes identified by the method described herein. In some embodiments, each novel synthetic bioactive polypeptide comprises a randomly generated polypeptide sequence in addition to at least one or at least two epitope sequences. In some embodiments, the randomly generated sequence is 3, 6, 9, or 12 amino acids in length. In a preferred embodiment, each novel synthetic bioactive polypeptide sequence comprise two 3 amino acid epitope sequences identified by the method disclosed herein, and at least one randomly generated polypeptide sequence to generate a 12 amino acid novel synthetic bioactive polypeptide sequence. In one embodiment, the novel synthetic bioactive polypeptide sequence is selected from SEQ ID NO: 1-172. In one embodiment, a plurality of novel synthetic bioactive polypeptide sequences is synthesized on an array for contact with a sample to determine sensitivity and specificity of each novel synthetic bioactive polypeptide sequence for detection of a sample with an autoimmune disorder. In one embodiment, novel synthetic bioactive polypeptides with a high sensitivity and/or specificity for detection of an autoimmune disorder are selected for further modification of random polypeptide sequence around the epitopes contained therein for screening on another polypeptide array. The methods described herein result in the generation of bioactive polypeptide sequences that act as epitopes for binding to an antibody associated with an autoimmune disease having a high sensitivity and/or specificity.

In one embodiment, a polypeptide array is generated with a plurality of synthetic bioactive polypeptide sequence provided herein. In one embodiment, the array has at least 4, 5, 6, 7, 8, 9, 10, 20, 30, 40, 50, 60, 70, 80, 90, or 100 novel synthetic bioactive polypeptide sequences generated by the methods disclosed herein. In one embodiment, the array has at least 4, 5, 6, 7, 8, 9, 10, 20, 30, 40, 50, 60, 70, 80, 90, or 100 polypeptides with a sequence selected from the group consisting of SEQ ID NO: 1-172. In one embodiment, the polypeptide array has a sensitivity of detection of an autoimmune disorder in a subject suspected of having the autoimmune disorder of greater than 90%, 91%, 92%, 93%, 94%, 95%, 96%, 97%, 98%, or 99%. In one embodiment, the polypeptide array has a specificity of detection of an autoimmune disorder in a subject suspected of having the autoimmune disorder of greater than 90%, 91%, 92%, 93%, 94%, 95%, 96%, 97%, 98%, or 99%.

Peptide Sequences and Methods of Use

Arrays

Also disclosed herein are methods of using substrates, formulations, and/or arrays. Uses of the arrays disclosed herein can include research applications, therapeutic purposes, medical diagnostics, and/or stratifying one or more patients.

Any of the arrays described herein can be used as a research tool or in a research application. In one aspect, arrays can be used for high throughput screening assays. For example, enzyme substrates (i.e., peptides on a peptide array described herein) can be tested by subjecting the array to an enzyme and identifying the presence or absence of enzyme substrate(s) on the array, e.g., by detecting at least one change among the features of the array.

Arrays can also be used in screening assays for ligand binding, to determine substrate specificity, or for the identification of peptides that inhibit or activate proteins. Labeling techniques, protease assays, as well as binding assays useful for carrying out these methodologies are generally well-known to one of skill in the art.

In some embodiments, an array can be used to represent a known protein sequence as a sequence of overlapping peptides. For example, the amino acid sequence of a known protein is divided into overlapping sequence segments of any length and of any suitable overlapping frame, and peptides corresponding to the respective sequence segments are in-situ synthesized as disclosed herein. The individual peptide segments so synthesized can be arranged starting from the amino terminus of the known protein.

In some embodiments, an array is used in a method wherein the antigenic representation of the array includes at least one region where the whole antigen sequence of a known protein is spanned via epitope sliding; the immunoactive regions of the antigen are determined by contacting one or more clinical samples on the array or a plurality of different arrays, and the set of peptide sequences required to represent the known protein antigen are reduced.

In some embodiments, a sample is applied to an array having a plurality of random peptides. The random peptides can be screened and BLASTed to determine homologous domains with, e.g., a 90% or more identity to a given antigenic sequence. In some aspect, the whole antigenic sequence can then be synthesized and used to identify potential markers and/or causes of a disease of interest.

In some embodiments, an array is used for high throughput screening of one or more genetic factors. Proteins associated with a gene can be a potential antigen and antibodies against these proteins can be used to estimate the relation between gene and a disease.

In another example, an array can be used to identify one or more biomarkers. Biomarkers can be used for the diagnosis, prognosis, treatment, and management of diseases. Biomarkers may be expressed, or absent, or at a different level in an individual, depending on the disease condition, stage of the disease, and response to disease treatment. Biomarkers can be, e.g., DNA, RNA, proteins (e.g., enzymes such as kinases), sugars, salts, fats, lipids, or ions.

Arrays can also be used for therapeutic purposes, e.g., identifying one or more bioactive agents. A method for identifying a bioactive agent can comprise applying a plurality of test compounds to an array and identifying at least one test compound as a bioactive agent. The test compounds can be small molecules, aptamers, oligonucleotides, chemicals, natural extracts, peptides, proteins, fragment of antibodies, antibody like molecules or antibodies. The bioactive agent can be a therapeutic agent or modifier of therapeutic targets. Therapeutic targets can include phosphatases, proteases, ligases, signal transduction molecules, transcription factors, protein transporters, protein sorters, cell surface receptors, secreted factors, and cytoskeleton proteins.

In another aspect, an array can be used to identify drug candidates for therapeutic use. For example, when one or more epitopes for specific antibodies are determined by an assay (e.g., a binding assay such as an ELISA), the epitopes can be used to develop a drug (e.g., a monoclonal neutralizing antibody) to target antibodies in disease.

In one aspect, also provided are arrays for use in medical diagnostics. An array can be used to determine a response to administration of drugs or vaccines. For example, an individual's response to a vaccine can be determined by detecting the antibody level of the individual by using an array with peptides representing epitopes recognized by the antibodies produced by the induced immune response. Another diagnostic use is to test an individual for the presence of biomarkers, wherein samples are taken from a subject and the sample is tested for the presence of one or more biomarkers.

Arrays can also be used to stratify patient populations based upon the presence or absence of a biomarker that indicates the likelihood a subject will respond to a therapeutic treatment. The arrays can be used to identify known biomarkers to determine the appropriate treatment group. For example, a sample from a subject with a condition can be applied to an array. Binding to the array may indicate the presence of a biomarker for a condition. Previous studies may indicate that the biomarker is associated with a positive outcome following a treatment, whereas absence of the biomarker is associated with a negative or neutral outcome following a treatment. Because the patient has the biomarker, a health care professional may stratify the patient into a group that receives the treatment.

In some embodiments, a method of detecting the presence or absence of a protein of interest (e.g., an antibody) in a sample can include obtaining an array disclosed herein and contacted with a sample suspected of comprising the protein of interest; and determining whether the protein of interest is present in the sample by detecting the presence or absence of binding to one or more features of the array. In some embodiments, the protein of interest can be obtained from a bodily fluid, such as amniotic fluid, aqueous humour, vitreous humour, bile, blood serum, breast milk, cerebrospinal fluid, cerumen, chyle, endolymph, perilymph, feces, female ejaculate, gastric acid, gastric juice, lymph, mucus, peritoneal fluid, pleural fluid, pus, saliva, sebum, semen, sweat, synovial fluid, tears, vaginal secretion, vomit, or urine.

In some embodiments, a method of identifying a vaccine candidate can include obtaining an array disclosed herein contacted with a sample derived from a subject previously administered the vaccine candidate, wherein the sample comprises a plurality of antibodies; and determining the binding specificity of the plurality of antibodies to one or more features of the array. In some embodiments, the features comprise a plurality of distinct, nested, overlapping peptide chains comprising subsequences derived from a source protein having a known sequence.

Also disclosed herein are methods for manufacturing arrays. In some embodiments, the arrays disclosed herein can be synthesized in situ on a surface, e.g., a substrate disclosed herein. In some instances, the arrays are made using photolithography. For example, masks can be used to control radiation or light exposure to specific locations on a surface provided with linker molecules having protecting groups. In the exposed locations, the protecting groups are removed, resulting in one or more newly exposed reactive moieties on the linker. The surface is then contacted with a solution containing a coupling molecule. The coupling molecule can have at least one site that is reactive with the newly exposed reactive moiety on the linker and at least a second reactive site protected by one or more protecting groups. The desired coupling molecule is then coupled to the unprotected linker molecules. The process can be repeated to synthesize a large number of features in specific or positionally-defined locations on a surface (see, for example, U.S. Pat. No. 5,143,854 to Pirrung et al., U.S. Patent Application Publication Nos. 2007/0154946 (filed on Dec. 29, 2005), 2007/0122841 (filed on Nov. 30, 2005), 2007/0122842 (filed on Mar. 30, 2006), 2008/0108149 (filed on Oct. 23, 2006), and 2010/0093554 (filed on Jun. 2, 2008), each of which is herein incorporated by reference). Other preferred methods and compositions useful for synthesizing features on an array, including fusion peptides described herein, is disclosed in PCT Publication No. WO 2016/040703, "Peptide Microarrays and Novel Biomarkers For Celiac Disease," published Mar. 17, 2016, incorporated by reference herein in its entirety.

Vaccines and Administration

The invention also provides a vaccine comprising sequences of a synthetic polyepitope-containing peptide, a biologically active fragment or variant thereof, and/or a polynucleotide encoding one or more thereof. Also provided is a vaccine comprising a peptide of the invention and/or a polynucleotide of the invention. Several embodiments of vaccines and vaccine administration can be found in PCT Publication No. WO 2016/040703, "Peptide Microarrays and Novel Biomarkers For Celiac Disease," published Mar. 17, 2016, incorporated by reference herein in its entirety.

EXAMPLES

The following examples illustrates a method of identifying biomarkers for Celiac diseases. The biomarkers include a set of peptides obtained from known antigens in Celiac disease, including, but not limited to alpha, beta, gamma, and omega gliadin, the deamidated modification thereof, and tTG. The method includes synthesizing a peptide library of 12-mer peptides based on these known Celiac antigens. In some embodiments, sequences of the 12-mer peptides are identified by shifting through the amino acid sequences of the known Celiac antigens by either two or three amino acid at a time. FIG. 2A illustrates identifying 12-mer sequences based on shifting by two amino acids along the alpha/beta gliadin sequence. Identification of 12-mer sequences of tTG is not explicitly depicted here, though they can be obtained though a similar approach as done for gliadin peptides. FIG. 2B illustrates deamidating the 12-mer GPs one or two glutamines at a time to increase the size of the DGP portion of the peptide library. The peptide library was then synthesized on a microarray, as described in more detail below. The coupling yield during synthesis of the peptides on the array was continually monitored for peptide yield, purity and sequence fidelity using fluorescence, mass spectrometry, and monoclonal antibody binding substrate assays. To identify biomarkers based on B cell epitopes of tTGs and DGPs, peptide microarrays including 2.1 million different peptides from the tTG and DGP peptide library, including triple duplicates of each peptide, were synthesized, picked and placed onto 96 pillar plates.

Example 1: Wafer Substrate Preparation

Prime grade 300 mm silicon wafers, having p-type boron, (1,0,0)-Orientation, 1-5 Ohm/cm and 725 μm thickness, were obtained from Process Specialties. The wafers were deposited with 1000 Å thermal oxide by dry oxidation at 10000 Celsius in a furnace under pure oxygen atmosphere for 2 hours. Commercial photoresist P5107 was spin coated on the wafers at 2000 rpm for 40 seconds using the Sokudo RF3S Coat/Develop Track. The wafers were exposed with an inverse zero layer mask using the Nikon NSR S205 KrF Scanner at a wavelength of 248 nm. This was followed by post exposure bake at 110° Celsius for 90 seconds and then developed using the developer NMD-3 at 2.38% (TOK America). Oxide etching was performed by wet oxide etch of the wafers using buffered hydrofluoric acid which was prepared by mixing 5 parts of 40 weight % of ammonium fluoride (Sigma) with 1 part of 49 weight % of hydrofluoric acid (Sigma) for 1 minute. The wafers were then stripped with Nanostrip (CyanTek) for 24 hours, finally washed with DI Water, and sonicated in DI Water for 10 minutes. This process as illustrated in FIG. 3A resulted in a substrate with a feature area that measured a height of 1000 Å containing thermal oxide while containing silicon in the non-feature area.

A DI 5000 AFM system was used to measure the roughness and calculate the density of the substrate. FIG. 3B shows the pillars and their dimensions formed after the process described above and illustrated in FIG. 3A. FIG. 3C illustrates the root mean square (RMS) roughness of the substrate. The density of the substrate was calculated to be approximately 100-150 pM.

Example 2: Wafer Surface Derivatization

Wafers were copiously washed with DI water for 5 minutes and spin coated with a solution containing 1.25% (v/v) of 3-aminopropyltriethoxysilane [APTES](Sigma Aldrich) in N-methyl-pyrollidone [NMP](BDH) and left at room temperature for 15 minutes. Curing of the wafers was done at 1200 Celsius for 60 minutes under $N_2$ atmosphere. Wafers were then spin coated with a coupling solution containing 2 weight % of Fmoc-Gly-OH (Anaspec), 2 weight % of HOBt (Anaspec) and 2 weight % of N,N'-diisopropylcarbodiimide [DIC](Sigma Aldrich) in NMP and baked at 60° Celsius for 5 minutes. This enabled coupling of Fmoc-Glycine to the free amine present in APTES. Wafers were then rinsed with NMP and then capped with 50% (v/v) of Acetic Anhydride mixed with 50% of NMP to cap any remaining free amines which have not been coupled. Wafers were stripped with acetone (BDH) and isopropyl alcohol [IPA](BDH). Fmoc protection of glycine was removed by spin coating the wafer with 5% (v/v) of piperidine (Sigma Aldrich) in NMP and baking at 800 Celsius for 300 seconds. The linker Fmoc-$(PEG)_4$—COOH (Anaspec) was then coupled to the wafer surface by spin coating a coupling solution containing 2 weight % of the linker, 2 weight % of HOBt (Anaspec) and 2 weight % of N,N'-diisopropylcarbodiimide [DIC] in NMP and baked at 900 Celsius for 120 seconds. Wafers were then rinsed with NMP and subsequently capped with 50% (v/v) of acetic anhydride mixed with 50% of NMP to cap any remaining free amines. Wafers were stripped with acetone and IPA to complete the surface derivatization process.

Example 3: Peptide Array Synthesis

The steps performed for synthesizing the peptides on the array are illustrated in FIG. 4 and described in detail above.
Activation Solution An amino acid activation solution was prepared as follows: 1% by weight of poly(methyl methacrylate) [PMMA] (Polysciences) was dissolved in N-methyl pyrollidone by sonication for 10 minutes. 2% by weight of Fmoc-amino acid (Anaspec) was then added to the solution followed by addition of 2% by weight of HOBt (Anaspec). Finally, 1% by weight of tetrazole thione was added to the solution. The solution was then filtered using a 0.05 μm filtration setup.
Carbodiimide Formation Mechanism The photo activated carbodiimide coupling was performed as follows:

Tetrazole thiones were used that upon exposure at 248 nm undergo a ring opening mechanism and release a carbodiimide that activates the carboxylic acid groups of amino acids being coupled to the wafer. Esters of -OBt or -OAt were formed upon addition of HOBt or HOAt. Thus, tetrazole thiones at 248 nm were used to photoactivate an amino acid to form a stable ester for efficient coupling.
Amino Acid Coupling A base resist solution containing 1 weight % of polymer and 3 weight % of piperidine dissolved in NMP was spin coated onto the wafer at 3000 rpm for 30 seconds and soft baked at 650 Celsius for 1 minute in a hot plate. Now the wafer was baked at 800 Celsius for 300 seconds. Fmoc protection was removed in all features leaving the unprotected amine group. The incoming amino acid activation solution was spin coated onto a wafer at 3000 rpm for 30 seconds and soft baked at 650 Celsius for 1 minute in a hot plate. Now the wafer was exposed using a reticle which exposes desired features for which the incoming amino acid needs to be coupled at an exposure dose of 120 mJ/$cm^2$ and then hard baked at 850 Celsius for 90 seconds in a hot plate. As described above, tetrazole thione upon exposure releases a carbodiimide and selective activation of amino acid was achieved in the exposed features. Therefore, the incoming Fmoc-protected amino acid present in the activation solution was activated and coupled to the unprotected amine present on the wafer in the same step completing the coupling of one layer of amino acid. Each coupling layer comprises reticles for each incoming Fmoc amino acid to be coupled, which expose features independent of the other reticles used for the same layer. After coupling all amino acids for a particular layer, the wafer was then spin coated with a solution of 50 weight % of NMP and 50 weight % of acetic anhydride to cap any remaining unprotected amine of the wafer that had no amino acid coupled for this particular layer. The wafer was stripped in acetone and IPA to remove any base resist present on the surface after each step. The whole process was repeated for each individual coupling layer of amino acids designed to be coupled to complete the synthesis of peptide chains attached to the array surface.

Side Chain Protection Removal

After the completion of peptide synthesis, any remaining side group protections present for any coupled amino acids were removed to enable biological activity of the peptide. A side chain protection removal solution was prepared by mixing 95 weight % trifluoroacetic acid [TFA](Sigma Aldrich) and 5 weight % DI water. The wafers were reacted with the side chain protection removal solution for 90 mins. This step was followed by washing the wafer successively with TFA (for 5 mins), IPA (for 5 mins), NMP (for 5 mins), neutralize with 5 weight % of DIEA (Alfa Aesar) in NMP (for 5 mins), and followed by washing the wafer successively with NMP (for 5 mins) and IPA (for 5 mins).

Example 4: Creation of Novel, Synthetic CeD Biomarkers from Combinations of tTG-DGP Complexes for CeD Diagnosis To identify novel biomarkers for CeD, serum samples were collected from an exploratory cohort of 90 patients with biopsy-proven CeD, and from 79 healthy control patients.[3] The clinical characteristics of the exploratory cohort are depicted in Table 2 Å below.

TABLE 2A

| Clinical characteristics of the exploratory cohort | | | | | |
|---|---|---|---|---|---|
| | | AGE | | SEX | |
| Group | N | MEAN | RANGE | MALE | FEMALE |
| CeD | 90 | 39.4 | 19.5-60.2 | 43% | 57% |
| Healthy controls | 79 | 40.2 | 19.7-63.3 | 48% | 52% |

Serum samples were also collected from a validation cohort of 82 patients with diagnosed CeD and 217 control patients. The clinical characteristics of the validation cohort are depicted in Table 2B below. The validation cohort was used to verify the diagnostic utility of the biomarker discovered in the exploratory cohort. Among the 82 patients with diagnosed CeD in the validation cohort, 4 patients with IgA-deficiency were included.

TABLE 2B

| Clinical characteristics of the validation cohort | | | | | |
|---|---|---|---|---|---|
| | | AGE | | SEX | |
| Group | N | MEAN | RANGE | MALE | FEMALE |
| CeD | 82 | 47.7 | 34.0-59.0 | 28.0% | 72.0% |
| Healthy controls | 217 | 35.6 | 26.6-44.6 | 40.1% | 59.9% |

For solid-phase peptide synthesis, silicon-based wafers (300 mm diameters)—with a 100-nm-tall, thermal oxide-coated feature area and non-feature area containing silicon—were made using photolithography and an inductively coupled plasma deep-etching technique. The surface of the prepared silicon-based wafer contained a monolayer of aminosilane that provided peptide attachment sites, in which peptide synthesis was performed using fluorenylmethoxy-carbonyl (Fmoc) chemistry. After Fmoc protection was removed, the unprotected amine was coupled with the incoming desired Fmoc amino acid using a specific reticle that activates only the desired site where the incoming amino acid needs to be coupled. The process was repeated for each individual layer of amino acids to create the desired peptide sequences at each feature area.

A set of approximately 66,000 12-mer peptides, with sequences from a lateral shift of 2 amino acids in α, β, γ, and Ω fractions of gliadin, were synthesized on silicon-based wafers. In addition, in these synthetic GPs, each glutamic acid was replaced in the position of glutamine, mimicking the deamidation of GPs (DGPs). The peptide microarray immunoassay was used to assess native peptides, DGPs, and key 3-mer GP sequences with high antibody-binding intensity associated with CeD.[3] Overlapping 12-mer peptides and various lengths of tTG were also synthesized according to a scheme similar to that for GPs. In addition, novel combined sequences—which were combinations of key 3-mer GP sequences and tTG subsequences—were synthesized on the silicon-based wafers. For example, in the new combined sequence YGDGVSQPEQPF (SEQ ID NO: 173), YGDGVS (SEQ ID NO: 174) is from tTG (positions 245-250) and QPE and QPF are key 3-mer GP sequences. A method for selecting the new combined tTG-DGP sequences is shown in FIG. 5.

FIG. 5 depicts examples of combined epitopes of the tTG-DGP complex, in accordance with an embodiment. Specifically, FIG. 5 depicts examples of 3 different ways to combine tTG and GP segments. YGDGVS (SEQ ID NO: 174) is located at positions 245 to 250 of the tTG peptide, and PEQ and PEP are 2 key 3-mer amino acids of GP. Upper row 1, YGDGVS (SEQ ID NO: 174) is followed by PEQ and PEP. Middle Row, YGDGVS (SEQ ID NO: 174) is located between PEQ and PEP. Lower Row, PEQ and PEQP (SEQ ID NO: 175) are followed by YGDGVS (SEQ ID NO: 174). E indicates glutamic acid; tTG, tTG; Q, glutamine; Y, Tyrosine; D, Aspartate; G, Glycine; V, Valine; P, Proline; F, Phenylalanine; S, Serine.

A fluorescent peptide microarray platform was used to estimate the antibody-binding intensity of each novel synthesized tTG-DGP neoepitope. The region of interest stitching program using JAVA transformed an image file from the scan of a peptide microarray chip to individual antibody-binding intensity values, which were calculated using the median foreground intensity and then applying binary log transformation to stabilize variance. Each antibody-binding intensity value is linked to a corresponding peptide sequence.

A random forest model was used to remove the unreliable peptide sequences of the tTG-DGP complex.[16] A random forest classifier was trained to detect areas of peptide sequences with values that were not within the 95% linear regression confidence band of a single linear regression analysis of multiple assays (performed using the rapmad [Robust Analysis of Peptide MicroArray Data]R-package).[17] Furthermore, background normalization modeling was also applied-which was performed using an expectation-maximization algorithm (performed using R-package) that placed blank spots where no sequences were synthesized.

After eliminating background noise and unreliable peptide sequences, support vector machine modeling[18] was applied to a training set of approximately 55,000 to construct a hyperplane and maximize the margins of the training data between the 2 classes (CeD vs no CeD) (performed using the Python package), with the aim of identifying the disease-associated peptide sequences of the tTG-DGP complex. Based on results of the support vector machine training, the identified disease-associated peptide sequences were then tested on unknown samples to compute the prediction accuracy, sensitivity, and specificity. Further receiver operating characteristic (ROC) curve analysis was performed to determine the sensitivity and specificity of each peptide. The threshold value for the ROC curve of each peptide was determined by choosing the value with the highest sensitivity and specificity. Furthermore, principal component analysis, hierarchical cluster analysis with heat maps, and random forest multivariate analysis were performed using R- or Python package.[19]

Example 5: Correlation Between Immune Reactivity of Novel, Synthetic CeD Biomarkers with CeD Severity The synthesized tTG peptide fragments were tested in serum samples from the exploratory cohort to determine significantly increased in the serum samples of the patients with CeD, but immune reactivity was minimal or nearly 0 in controls.

In the exploratory cohort, the identified set of neoepitopes derived from the tTG-DGP complex showed very high sensitivity (99%) and specificity (100%) for diagnosing CeD. To validate the discriminative power of this tTG-DGP complex set, serum samples from the validation cohort of 82 patients with CeD and 217 control patients were assayed in a blind test. This tTG-DGP complex set showed high accuracy for distinguishing CeD cases from controls, achieving 99% sensitivity and 100% specificity. In particular, compared with current serologic tests for CeD including tTG-IgA and DGP-IgA (specifically the tTG-IgA and the DGP-IgA ELISA tests), sensitivity and specificity were higher when using these neoepitopes to differentiate CeD cases from controls. Table 3 below compares sensitivity, specificity, overall accuracy, positive predictive value (PPV), and negative predictive value (NPV) of the neoepitopes of the tTG-DGP complex with current serologic tests for CeD, including the tTG-IgA and the DGP-IgA ELISA tests, in diagnosis of CeD. Overall, the neoepitopes of the tTG-DGP complex showed comparable or even higher diagnostic accuracy for discriminating CeD than clinically available serologic tests.

TABLE 3

Predictive value of tTG-DGP complex against current serodiagnostic tests for CeD diagnosis

| Peptide/Protein | Sensitivity % (95% CI) | Specificity % (95% CI) | Overall Accuracy % (95% CI) | Positive Predictive Value (PPV) | Negative Predictive Value (NPV) |
|---|---|---|---|---|---|
| tTG-DGP complex | 99 (93-100) | 100 (98-100) | 99 (98-100) | 1 | 0.99 |
| tTG-IgA[a] | 90 (82-95) | 99 (96-100) | 97 (94-98) | 0.97 | 0.96 |
| DGP IgA (ELISA) | 91 (83-96) | 97 (94-98) | 97 (94-98) | 0.96 | 0.97 | immune reactivity against tTG fragments. FIGS. 6A-B depict heat maps showing immune reactivity against tTG and the tTG-DGP complex, in accordance with an embodiment. Specifically, FIG. 6A depicts immune reactivity against the tTG peptide, in accordance with an embodiment. No significant differences in immune reactivity were found between the serum samples from patients with CeD and control patients.

The 12-mer synthesized neoepitopes derived from tTG and key 3-mer motifs of native peptides or DGPs were also tested in the serum samples of the exploratory cohort to identify immunogenic epitopes, which were defined as any sequence with an area under the ROC curve value >0.7. A total of 172 immunogenic epitopes of the tTG-DGP complex were identified. The sequence of each of the 172 immunogenic epitopes of the tTG-DGP complex that were identified is listed in Table 1 above. As discussed above, each epitope in Table 1 demonstrates high sensitivity and specificity for diagnosing CeD in healthy control patients, and has an area under the ROC curve >0.7.

FIG. 6B depicts immune reactivity against the neoepitopes of the tTG-DGP complex, in accordance with an embodiment. As shown in FIG. 6B, the antibody-binding intensity of the neoepitopes of the tTG-DGP complex was To compare the immune reactivity against epitopes of DGP, tTG, and tTG-DGP complex, we tested serum samples of selected disease controls who had villous atrophy without CeD, composed of 10 patients with autoimmune enteropathy, 6 patients with CVID associated enteropathy, and 11 patients with drug-induced enteropathy. We found that the immune reactivity against neoepitopes of tTG-DGP complex in these disease controls was significantly lower than in patients with CeD and was similar to other control patients. Additionally, 4 patients with complete IgA deficiency were included in CeD patients in the validation set. All these patients were negative for tTG-IgA, but immune reactivity against neoepitopes of tTG-DGP complex in these IgA deficient patients were increased, in particular IgG immune reactivity. Furthermore, patients who had intestinal villous atrophy but no CeD showed no immune reactivity against the neoepitopes of tTG-DGP complex.

Example 6: Evaluation of Novel, Synthetic CeD Biomarkers to Determine Healing Status in Patients with CeD Adhering to a GFD To evaluate the identified biomarkers for identifying mucosal healing status in patients with treated CeD, serum samples were collected from patients with treated and healed CeD mucosa (n=85), patients with treated but unhealed CeD mucosa (n=81), patients with untreated CeD mucosa (n=82), disease control patients (n=27), and healthy control patients (n=217). Mucosal healing status was defined by persistent villous atrophy despite adhering to a GFD or histologic recovery (no villous atrophy). Unhealed patients with CeD Patients with refractory CeD were not included in this study. The mucosal healing status in small intestine was classified based on the pathologic reports; treated CeD patients who had partial or total villous atrophy were categorized into treated but unhealed CeD group. Disease control patients were defined by villous atrophy without CeD. The 27 disease control patients included 10 patients with autoimmune enteropathy, 6 patients with common variable immunodeficiency-associated enteropathy, and 11 patients with drug-induced enteropathy.

Table 4 shows the characteristics of treated patients with CeD according to mucosal healing status. Patients with treated and healed CeD mucosa were younger on average than patients with treated but unhealed CeD mucosa, but similar with regard to sex (73% vs 72% of patients were women, respectively). Patients with treated but unhealed CeD mucosa adhered to a GFD longer than patients with treated and healed CeD, but this was not statistically significant (P=0.16). While 7% of patients with treated and healed CeD mucosa were positive to tTG-IgA, 27% of patients with treated but unhealed CeD mucosa were positive for tTG-IgA and about three-quarters of patients with treated but unhealed CeD mucosa were negative. In addition, 48% of patients with treated but unhealed CeD mucosa were positive for DGP-IgA and 9% of patients with treated but healed CeD mucosa were positive for DGP-IgA.

TABLE 4

Characteristics of Healed and Unhealed patients treated for CeD

| Characteristic | Treated/Healed Celiac Disease Mucosa (n = 85) | Treated/Unhealed CeD Mucosa (n = 81) | P Value |
|---|---|---|---|
| Age at diagnosis, mean (SD), y | 41.1 (15.2) | 47.5 (15.5) | <.001 |
| Female sex, % | 73 | 72 | .60 |
| Duration of GFD, median (interquartile range), y | 2.8 (1.7-5.1) | 3.5 (1.8-8.1) | .16 |
| tTG-IgA positivity, % | 7 | 27 | <.001 |
| DGP-IgA positivity, % | 9 | 48 | <0.001 |
| Partial or total villous atrophy, % | 0 | 100 | <0.001 |

FIGS. 7A-B depict immune reactivity against epitopes of the tTG-DGP complex based on antibody-binding intensity, in accordance with an embodiment. More specifically, FIGS. 7A-B depict immune reactivity against the neoepitopes of the tTG-DGP complex in patients with treated CeD according to healing status. FIG. 7A depicts immune reactivity against epitopes of the tTG-DGP complex in patients with untreated CeD, treated but unhealed CeD, and treated and healed CeD, and in healthy control patients, in accordance with an embodiment. As shown in FIG. 7A, patients with untreated CeD and with treated but unhealed CeD show higher antibody-binding intensity relative to healthy control patients, patients with treated and healed CeD, and disease control patients with villous atrophy due to autoimmune enteropathy, common variable immunodeficiency associated enteropathy, or drug-induced enteropathy.

FIG. 7B depicts principal component analysis of immune reactivity against neoepitopes of the tTG-DGP complex, in accordance with an embodiment. Specifically, FIG. 7B illustrates the correlation between the level of immune reactivity against the tTG-DGP complex and CeD phenotype. Patients with treated and healed CeD and healthy controls patients appear together on the PCA plot.

Overall, as shown in the FIG. 7A, immune reactivity against the neoepitopes of the DGP-tTG complex was stronger in patients with treated but unhealed CeD mucosa than patients with treated and healed CeD mucosa and control patients. The average antibody-binding intensity of the neoepitopes derived from the tTG-DGP complex significantly differed among the 5 groups (P<0.001). Immune reactivity decreased stepwise according to intestinal mucosal damage status, showing the highest mean (SD) reactivity in the patients with untreated CeD mucosa (32.5 [16.4]) followed by patients with treated but unhealed CeD mucosa (15.1 [7.5]), patients with treated and healed CeD mucosa (5.5 [3.4]), control patients (1.3 [0.5]), and disease controls (1.3 [0.4]). Furthermore, in the principal component analysis shown in FIG. 7B, the patients with treated and healed CeD mucosa and control patients were closely aggregated but the patients with treated but unhealed CeD mucosa and patients with untreated CeD mucosa were similarly distributed.

FIG. 8 depicts a comparison of antibody-binding levels of tTG-immunoglobulin A complex and antibody-binding levels of tTG-DGP complex in patients with treated but unhealed CeD, in accordance with an embodiment. More specifically, FIG. 8 shows that the neoepitopes of the tTG-DGP complex can diagnose treated but unhealed CeD mucosa compared with the tTG-IgA enzyme-linked immunosorbent assay (ELISA) test. Although about 75% of patients with treated but unhealed CeD tested negative for tTG-IgA, most of these patients showed increased immune reactivity against the neoepitopes of the tTG-DGP complex. Table 5 below compares sensitivity, specificity, overall accuracy, positive predictive value (PPV), and negative predictive value (NPV) of the neoepitopes of the tTG-DGP complex with current serologic tests for CeD, including the tTG-IgA and the DGP-IgA ELISA tests, in identification of healing status in patients with treated but unhealed CeD. Compared with the tTG-IgA ELISA test (specifically the tTG-IgA and the DGP-IgA ELISA tests), the neoepitopes of the tTG-DGP complex showed higher sensitivity (84%) and specificity (95%) with a positive predictive value of 0.94 and a negative predictive value of 0.86 for identifying healing status in patients with treated but unhealed CeD mucosa.

TABLE 5

Predictive value of tTG-DGP complex against current serodiagnostic tests for identification of treated CeD healing status

| Peptide/ Protein | Sensitivity % (95% CI) | Specificity % (95% CI) | Overall Accuracy % (95% CI) | Positive Predictive Value (PPV) | Negative Predictive Value (NPV) |
|---|---|---|---|---|---|
| tTG-DGP complex | 84 (74-90) | 95 (88-98) | 90 (84-94) | 0.94 | 0.86 |
| tTG-IgA | 27 (19-38) | 93 (85-97) | 61 (53-68) | 0.78 | 0.57 |
| DGP-IgA | 48 (38-59) | 91 (83-95) | 70 (63-76) | 0.83 | 0.64 |

The biomarker discovery via the platform of highly efficient mass manufacturing of ultra high density peptide microarrays presented here provides an efficient method to determine novel epitopes through mapping of antigens and combining the immunopotent sequences. Peptide miroarrays based on 2.1 million of 9-mer to 15-mer peptides, each overlapping with three or six amino acids, were used to cover the immunogenic proteins with very high density maximizing the ability to identify informative peptides, and showed the effectiveness and utility of this technology on identification of unknown but novel epitopes that are recognized by patients with autoimmune disease. An advantage of this method includes the development of more precise diagnostic tests that can be incorporated into panels of testing for autoimmune diseases, including Celiac disease. Moreover, the contribution of the individual amino acids of the antigen were evaluated for antibody binding, by designing microarrays of peptides containing lateral shifts of one amino acid, achieving higher mapping resolution for the target antigen.

All previous photolithography based microarray in situ synthesis methods[5, 22, 22-24] are based on individually addressable deprotection step and then monomers coupling to those selective deprotected sites. The methods described herein involve generalized de-protection followed by selective activation, providing two advantages: 1) a far higher fidelity of peptide synthesis, and 2) a greatly reduced time requirement for each step. This permits a significantly higher number of steps, as many as 400, in the synthesis of a peptide microarray, leading with a very low yield loss. In some embodiment, the combination of high-fidelity and shorter reaction times result in a much higher yield and the ability to generate a large number of chips. Additional advantages include the cost savings due to high-fidelity that may be required for diagnostic testing. The method described herein utilizes the state of the art 248 nm semiconductor lithography semiconductor tools on a proven 300 mm silicon wafer platform. In some embodiments, a very high microarray density enables not only the molecular diversity needed for biomarker discovery but also to enable large scale biomarker validation. The method is well suited for mass manufacturing for routine diagnostics since the chips size can scale down to 0.5×0.5 mm$^2$ fit any diagnostics well plate format, like 96, 384, 1396. This enables smaller size samples to be used for routine diagnostics.

The methods disclosed herein represent non-invasive, broadly available, low cost, and versatile methods by using the disclosed peptide microarrays, which are well-suited for routine health care diagnostic purposes and for providing a powerful novel tool for biomarker discovery.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

Finally, it should be noted that the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention.

REFERENCES

1. Rubio-Tapia A, Hill ID, Kelly C P, et al. ACG clinical guidelines: diagnosis and management of Celiac disease. Am J Gastroenterol 2013; 108:656-76; quiz 677.

2. Jabri B, Sollid L M. T Cells in Celiac Disease. J Immunol 2017; 198:3005-3014.

3. Choung R S, Marietta E V, Van Dyke C T, et al. Determination of B-Cell Epitopes in Patients with Celiac Disease: Peptide Microarrays. PLoS One 2016;11: e0147777.

4. Sulkanen S, Halttunen T, Laurila K, et al. Tissue transglutaminase autoantibody enzyme-linked immunosorbent assay in detecting Celiac disease. Gastroenterology 1998; 115:1322-8.

5. Walker M M, Murray J A, Ronkainen J, et al. Detection of Celiac disease and lymphocytic enteropathy by parallel serology and histopathology in a population-based study. Gastroenterology 2010; 139:112-9.

6. Cavell B, Stenhammar L, Ascher H, et al. Increasing incidence of childhood coeliac disease in Sweden. Results of a national study. Acta Paediatr 1992; 81:589-92.

7. Ludvigsson J F, Lebwohl B, Green PH. Amount May Beat Timing: Gluten Intake and Risk of Childhood Celiac Disease. Clin Gastroenterol Hepatol 2016; 14:410-2.

8. Myleus A, Ivarsson A, Webb C, et al. Celiac disease revealed in 3% of Swedish 12-year-olds born during an epidemic. J Pediatr Gastroenterol Nutr 2009; 49:170-6.

9. Molberg O, McAdam S, Lundin K E, et al. T cells from Celiac disease lesions recognize gliadin epitopes deamidated in situ by endogenous tissue transglutaminase. Eur J Immunol 2001; 31:1317-23.

10. Aleanzi M, Demonte A M, Esper C, et al. Celiac disease: antibody recognition against native and selectively deamidated gliadin peptides. Clin Chem 2001; 47:2023-8.

11. Sollid L M, Molberg 0, McAdam S, et al. Autoantibodies in coeliac disease: tissue transglutaminase—guilt by association?Gut 1997; 41:851-2.

12. Matthias T, Neidhofer S, Pfeiffer S, et al. Novel trends in Celiac disease. Cell Mol Immunol 2011; 8:121-5.

13. Bizzaro N, Tozzoli R, Villalta D, et al. Cutting-edge issues in Celiac disease and in gluten intolerance. Clin Rev Allergy Immunol 2012; 42:279-87.

14. Rubio-Tapia A, Hill I D, Kelly C P, et al. ACG clinical guidelines: diagnosis and management of Celiac disease. The American journal of gastroenterology 2013; 108:656-76; quiz 677.

15. Lebwohl B, Murray J A, Rubio-Tapia A, et al. Predictors of persistent villous atrophy in coeliac disease: a population-based study. Aliment Pharmacol Ther 2014; 39:488-95.

16. Breiman L. Random Forests. Machine Learning 2001; 45:5-32.

17. Renard B Y, Lower M, Kuhne Y, et al. rapmad: Robust analysis of peptide microarray data. BMC Bioinformatics 2011; 12:324.

18. Pedregosa F, Varoquaux G, Gramfort A, et al. Scikit-learn: Machine Learning in Python. Journal of Machine Learning Research 2011; 12:2825-2830.

19. Hilsenbeck S G, Friedrichs W E, Schiff R, et al. Statistical analysis of array expression data as applied to the problem of tamoxifen resistance. J Natl Cancer Inst 1999; 91:453-9.

20. Ciccocioppo R, Di Sabatino A, Ara C, et al. Gliadin and tissue transglutaminase complexes in normal and coeliac duodenal mucosa. Clin Exp Immunol 2003; 134:516-24.

21. van der Windt D A, Jellema P, Mulder C J, et al. Diagnostic testing for Celiac disease among patients with abdominal symptoms: a systematic review. JAMA 2010; 303:1738-46.

22. Health Quality O. Clinical utility of serologic testing for Celiac disease in ontario: an evidence-based analysis. Ont Health Technol Assess Ser 2010; 10:1-111.

23. Rashtak S, Ettore M W, Homburger H A, et al. Combination testing for antibodies in the diagnosis of coeliac disease: comparison of multiplex immunoassay and ELISA methods. Aliment Pharmacol Ther 2008; 28:805-13.

24. Sugai E, Selvaggio G, Vazquez H, et al. Tissue transglutaminase antibodies in Celiac disease: assessment of a commercial kit. Am J Gastroenterol 2000; 95:2318-22.

25. Hopper A D, Hadjivassiliou M, Hurlstone D P, et al. What is the role of serologic testing in Celiac disease?A prospective, biopsy-confirmed study with economic analysis. Clin Gastroenterol Hepatol 2008; 6:314-20.

26. Husby S, Koletzko S, Korponay-Szabo I R, et al. European Society for Pediatric Gastroenterology, Hepatology, and Nutrition guidelines for the diagnosis of coeliac disease. J Pediatr Gastroenterol Nutr 2012; 54:136-60.

27. Ludvigsson J F, Bai J C, Biagi F, et al. Diagnosis and management of adult coeliac disease: guidelines from the British Society of Gastroenterology. Gut 2014; 63:1210-28.

28. Ludvigsson J F, Agreus L, Ciacci C, et al. Transition from childhood to adulthood in coeliac disease: the Prague consensus report. Gut 2016; 65:1242-51.

29. Bai J C, Ciacci C, Corazza G R, et al. World Gastroenterology Organisation Practice Guidelines:Celiac Disease; World Gastroenterology Organisation: Milwaukee, WI, USA. 2016:1-35.

30. Skovbjerg H, Koch C, Anthonsen D, et al. Deamidation and cross-linking of gliadin peptides by transglutaminases and the relation to Celiac disease. Biochim Biophys Acta 2004; 1690:220-30.

31. Matthias T, Pfeiffer S, Selmi C, et al. Diagnostic challenges in Celiac disease and the role of the tissue transglutaminase-neo-epitope. Clin Rev Allergy Immunol 2010; 38:298-301.

32. Di Pisa M, Pascarella S, Scrima M, et al. Synthetic peptides reproducing tissue transglutaminase-gliadin complex neo-epitopes as probes for antibody detection in Celiac disease patients' sera. J Med Chem 2015; 58:1390-9.

33. Porcelli B, Ferretti F, Vindigni C, et al. Assessment of a Test for the Screening and Diagnosis of Celiac Disease. J Clin Lab Anal 2016; 30:65-70.

34. Lebwohl B, Granath F, Ekbom A, et al. Mucosal healing and risk for lymphoproliferative malignancy in Celiac disease: a population-based cohort study. Ann Intern Med 2013; 159:169-75.

35. Lebwohl B, Michaelsson K, Green P H, et al. Persistent mucosal damage and risk of fracture in Celiac disease. J Clin Endocrinol Metab 2014; 99:609-16.

36. Rubio-Tapia A, Rahim M W, See J A, et al. Mucosal recovery and mortality in adults with Celiac disease after treatment with a gluten-free diet. Am J Gastroenterol 2010; 105:1412-20.

37. Lebwohl B, Granath F, Ekbom A, et al. Mucosal healing and mortality in coeliac disease. Aliment Pharmacol Ther 2013; 37:332-9.

38. Rostom A, Murray J A, Kagnoff M F. American Gastroenterological Association (AGA) Institute technical review on the diagnosis and management of Celiac disease. Gastroenterology 2006; 131:1981-2002.

39. Institute AGA. AGA Institute Medical Position Statement on the Diagnosis and Management of Celiac Disease. Gastroenterology 2006; 131:1977-80.

40. Leonard M M, Weir D C, DeGroote M, et al. Value of IgA tTG in Predicting Mucosal Recovery in Children With Celiac Disease on a Gluten-Free Diet. J Pediatr Gastroenterol Nutr 2017; 64:286-291.

41. Silvester J A, Kurada S, Szwajcer A, et al. Tests for Serum Transglutaminase and Endomysial Antibodies Do Not Detect Most Patients With Celiac Disease and Persistent Villous Atrophy on Gluten-free Diets: a Meta-analysis. Gastroenterology 2017; 153:689-701 el.

42. Lanzini A, Lanzarotto F, Villanacci V, et al. Complete recovery of intestinal mucosa occurs very rarely in adult coeliac patients despite adherence to gluten-free diet. Aliment Pharmacol Ther 2009; 29:1299-308.

43. Kaukinen K, Collin P, Laurila K, et al. Resurrection of gliadin antibodies in coeliac disease. Deamidated gliadin peptide antibody test provides additional diagnostic benefit. Scand J Gastroenterol 2007; 42:1428-33.

44. Volta U, Granito A, Fiorini E, et al. Usefulness of antibodies to deamidated gliadin peptides in Celiac disease diagnosis and follow-up. Dig Dis Sci 2008; 53:1582-8.

45. Spatola B N, Kaukinen K, Collin P, et al. Persistence of elevated deamidated gliadin peptide antibodies on a gluten-free diet indicates nonresponsive coeliac disease. Aliment Pharmacol Ther 2014; 39:407-17.

46. Monzani A, Rapa A, Fonio P, et al. Use of deamidated gliadin peptide antibodies to monitor diet compliance in childhood Celiac disease. J Pediatr Gastroenterol Nutr 2011; 53:55-60.

47. McRae B L, Vanderlugt C L, Dal Canto M C, et al. Functional evidence for epitope spreading in the relapsing pathology of experimental autoimmune encephalomyelitis. J Exp Med 1995; 182:75-85.

48. Lehmann P V, Forsthuber T, Miller A, et al. Spreading of T-cell autoimmunity to cryptic determinants of an autoantigen. Nature 1992; 358:155-7.

49. Sohnlein P, Muller M, Syren K, et al. Epitope spreading and a varying but not disease-specific GAD65 antibody response in Type I diabetes. The Childhood Diabetes in Finland Study Group. Diabetologia 2000; 43:210-7.

50. Vincent A, Willcox N, Hill M, et al. Determinant spreading and immune responses to acetylcholine receptors in myasthenia gravis. Immunol Rev 1998; 164:157-68.

51. Vanderlugt C L, Miller S D. Epitope spreading in immune-mediated diseases: implications for immunotherapy. Nat Rev Immunol 2002; 2:85-95.

52. Sivalingam G N, Shepherd A J. An analysis of B-cell epitope discontinuity. Mol Immunol 2012; 51:304-9.

53. Forsstrom B, Axnas B B, Stengele K P, et al. Proteome-wide epitope mapping of antibodies using ultra-dense peptide arrays. Mol Cell Proteomics 2014; 13:1585-97.

We claim:

1. An array comprising an array surface and at least two linear peptide probes, wherein each of the at least two linear peptide probes comprises a binding motif selected from the group consisting of SEQ ID NOS: 1-172, and wherein the at least two peptide probes extend from the array surface.

2. The array of claim 1, wherein the array surface is a solid surface or a microparticle.

3. The array of claim 1, wherein the at least two peptide probes further comprise a label.

4. A peptide consisting of an amino acid sequence selected from the group consisting of SEQ ID NOS: 1-172.

5. The array of claim 1, wherein each of the at least two linear peptide probes comprises a binding motif selected from the group consisting of SEQ ID NOS: 1-119 and 121-172.

6. The peptide of claim 4, consisting of an amino acid sequence selected from the group consisting of SEQ ID NOS: 1-119 and 121-172.

* * * * *

SEQUENCE LISTING

<160> NUMBER OF SEQ ID NOS: 194

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Phe Glu Asp Gly Ile Leu Glu Gln Pro Pro Glu Gln
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Pro Phe Pro Gln Lys Thr Val Glu Ile Pro Glu Gln
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Phe Pro Leu Arg Asp Ala Pro Glu Gln Gln Pro Glu
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Phe Pro Gln Gln Pro Phe Trp Leu Thr Glu Gln Pro
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Phe Asp Val Phe Ala His Pro Phe Pro Phe Pro Gln
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

Ala Trp Cys Pro Ala Asp Phe Pro Glu Glu Gln Pro
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Phe Pro Glu Pro Ala Pro Ser Gln Glu Gln Pro Phe
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Glu Val Ser Leu Gln Glu Gln Pro Pro Glu Gln
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Glu Met Ile Trp Asn Phe Pro Phe Pro Glu Gln Pro
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Glu Gln Pro Pro Glu Gln Ala Glu Val Ser Leu Gln
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Phe Pro Glu Gln Pro Glu Tyr Gly Asp Gly Val Ser
1               5                   10

<210> SEQ ID NO 12

-continued

<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Pro Phe Pro Pro Glu Gln Ala Leu Leu Val Glu Pro
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

His Asp Gln Asn Ser Asn Gln Pro Phe Gln Pro Glu
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Pro Phe Pro Ser Val Asp Ile Leu Arg Gln Pro Glu
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Glu Gln Pro Leu Thr Gln Gln Gly Phe Glu Gln Pro
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Phe Pro Glu Phe Pro Glu Val Val Asn Phe Glu Ser
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

-continued

```
Gln Pro Phe Gln Pro Glu Tyr Asn Ser Ala His Asp
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asp Leu Cys Arg Glu Lys Pro Glu Gln Glu Gln Pro
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Glu Lys Leu Val Val Arg Pro Glu Gln Gln Pro Glu
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Phe Pro Gln Pro Gly Tyr Glu Gly Trp Glu Gln Pro
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Pro Glu Gln Pro Glu Tyr Gln Gly Ser Ser Phe
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Pro Phe Pro Asn Arg Ser Leu Ile Val Gln Pro Phe
1               5                   10

<210> SEQ ID NO 23
<211> LENGTH: 12
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 23

Asp Cys Thr Leu Ser Leu Pro Glu Gln Gln Pro Glu
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Pro Phe Pro Ser Val Asp Ser Leu Thr Phe Pro Glu
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Ala Val Glu Glu Gly Gln Pro Glu Pro Glu Gln
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Ser Thr Gly Tyr Gln Gln Pro Glu Pro Phe Pro
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Phe Glu Gly Arg Asn Tyr Phe Pro Glu Phe Pro Gln
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Glu Gln Pro Leu Gln Asn Pro Leu Pro Gln Pro Phe
1               5                   10

```
<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Trp Gln Ala Leu Asp Phe Pro Gln Pro Phe Pro
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Pro Glu Gln Arg Lys Leu Val Ala Glu Phe Pro Glu
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Pro Glu Pro Val Pro Val Arg Ala Phe Pro Gln
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Pro Phe Pro Gln Pro Phe Val Phe Ala Glu Val Asn
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Pro Phe Leu Ala Glu Arg Asp Leu Phe Pro Glu
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34
```

-continued

```
Pro Glu Gln Pro Glu Gln Val Asp Gln Gln Asp Cys
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Glu Gln Pro Ser Gly Met Val Asn Cys Glu Gln Pro
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Phe Pro Glu Leu Cys Ala Arg Thr Val Pro Phe Pro
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Pro Phe Pro Leu Leu Phe Asn Ala Trp Pro Phe Pro
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

His Leu Asn Lys Leu Ala Pro Glu Gln Gln Pro Glu
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Glu Gln Pro Asn Ala Pro Ile Gly Leu Pro Phe Pro
1               5                   10

<210> SEQ ID NO 40
<211> LENGTH: 12
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 40

Phe Pro Glu Arg Glu Ala Phe Thr Arg Glu Gln Pro
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Phe Pro Gln Pro Phe Pro Ala Ala Val Ala Cys Thr
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gln Pro Phe Pro Glu Gln Tyr Cys Cys Gly Pro Val
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Glu Gln Pro Gln Ser Met Asn Met Gly Pro Phe Pro
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Cys Arg Leu Leu Leu Cys Pro Glu Gln Pro Glu Gln
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ile Pro Thr Arg Val Val Phe Pro Glu Glu Gln Pro
1               5                   10
```

-continued

```
<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Pro Phe Leu His Met Gly Leu His Gln Pro Glu
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Pro Phe Pro Leu Ser Leu Glu Ala Ser Gln Pro Glu
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Phe Pro Gln Asn Gly Arg Asp His His Gln Pro Phe
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gln Pro Glu Asn Asn Thr Ala Glu Glu Phe Pro Glu
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Pro Phe Pro Leu Asp Pro Thr Pro Gln Gln Pro Phe
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 51

Ala His Ile Thr Asn Asn Glu Gln Pro Glu Gln Pro
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Phe Pro Gln Lys Val Arg Met Asp Leu Gln Pro Phe
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Phe Pro Glu Met Gly Ser Asp Phe Asp Gln Pro Phe
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Pro Glu Gln Lys Ser Val Gly Arg Asp Gln Pro Glu
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ile Lys Val Arg Ala Leu Pro Phe Pro Pro Glu Gln
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Phe Pro Glu Asn Phe His Cys Trp Val Pro Glu Gln
1               5                   10

<210> SEQ ID NO 57
<211> LENGTH: 12
<212> TYPE: PRT
```

-continued

```
<213> ORGANISM: Artificial Sequence
<220> FEATURE:
<223> OTHER INFORMATION: Description of Artificial Sequence: Synthetic
      peptide

<400> SEQUENCE: 57

Gly Arg Val Val Ser Gly Phe Pro Gln Gln Pro Phe
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gln Pro Glu Pro Phe Pro Ala Ser Thr Gly Tyr Gln
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ala Ala Val Ala Cys Thr Phe Pro Gln Pro Phe Pro
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Pro Phe Pro Pro Glu Gln Trp Met Thr Arg Pro Asp
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Pro Glu Gln Glu Gln Pro Trp Val Glu Ser Trp Met
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Pro Glu Pro Val Tyr Val Gly Arg Phe Pro Glu
1               5                   10
```

```
<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Pro Glu Gln Asn Tyr Glu Ala Ser Val Gln Pro Phe
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Glu Gln Pro Gln Pro Phe Val Val Asp Trp Ile Gln
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gln Pro Glu Gln Pro Glu Tyr Pro Glu Gly Ser Ser
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Pro Phe Pro Pro Lys Gln Lys Arg Lys Gln Pro Phe
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gln Pro Phe Asn Phe Gly Gln Phe Glu Glu Gln Pro
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 68

Gln Pro Glu Gln Pro Phe Val Asn Ala Asp Val Val
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ala Leu Leu Val Glu Pro Pro Phe Pro Pro Glu Gln
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Glu Gly Asp Leu Ser Thr Gln Pro Phe Gln Pro Phe
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Pro Glu Gln Asn Cys Asn Asp Asp Gln Gln Pro Phe
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Pro Phe Pro Thr Arg Ala Asn His Leu Pro Glu Gln
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Asp Gln Gly Val Leu Leu Pro Glu Gln Gln Pro Glu
1               5                   10

<210> SEQ ID NO 74
<211> LENGTH: 12

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Pro Glu Cys Gly Thr Phe Pro Gln Gln Pro Phe
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Phe Pro Gln Leu Val Leu Glu Arg Cys Gln Pro Phe
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gln Pro Phe Glu Gln Pro Val Val Thr Asn Tyr Asn
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Leu Tyr Arg Leu Ser Gln Pro Phe Glu Gln Pro
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ala Asp Ala Val Tyr Leu Pro Glu Gln Gln Pro Phe
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Phe Pro Gln Ser Glu Gly Thr Tyr Cys Gln Pro Glu
```

-continued

```
1               5                  10

<210> SEQ ID NO 80
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Phe Pro Gln Ser Asn Leu Leu Ile Glu Pro Glu Gln
1               5                  10

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Glu Asn Pro Glu Ile Lys Phe Pro Gln Pro Phe Pro
1               5                  10

<210> SEQ ID NO 82
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gln Pro Phe Gln Glu Tyr Val Leu Thr Phe Pro Gln
1               5                  10

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gln Pro Phe Ser Trp Ile Gly Ser Val Phe Pro Gln
1               5                  10

<210> SEQ ID NO 84
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Glu Asp Ile Thr His Thr Glu Gln Pro Gln Pro Phe
1               5                  10

<210> SEQ ID NO 85
<211> LENGTH: 12
<212> TYPE: PRT
<213> ORGANISM: Artificial Sequence
<220> FEATURE:
<223> OTHER INFORMATION: Description of Artificial Sequence: Synthetic
```

-continued

```
        peptide

<400> SEQUENCE: 85

Cys Gln Arg Val Lys Tyr Gln Pro Glu Pro Glu Gln
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 86

Glu Ile Pro Asp Pro Val Phe Pro Gln Gln Pro Glu
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 87

Glu Gly Ala Gly Leu Thr Gln Pro Glu Pro Glu Gln
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 88

Gln Pro Glu Ser Phe Val Leu Gly His Pro Glu Gln
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 89

Pro Glu Gln Lys Asn His Gly Cys Gln Glu Gln Pro
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 90

Pro Phe Pro Pro Gln Glu Lys Ser Glu Glu Gln Pro
1               5                   10

<210> SEQ ID NO 91
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gln Pro Phe Pro Val Glu Ala Gly Glu Phe Pro Glu
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Glu Gln Pro Met Ala Glu Glu Leu Val Phe Pro Glu
1               5                   10

<210> SEQ ID NO 93
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ile Lys Ile Arg Ile Leu Pro Phe Pro Pro Glu Gln
1               5                   10

<210> SEQ ID NO 94
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ile Leu Asp Ile Cys Leu Pro Phe Pro Phe Pro Gln
1               5                   10

<210> SEQ ID NO 95
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Phe Pro Glu Leu Thr Leu His Phe Glu Phe Pro Glu
1               5                   10

<210> SEQ ID NO 96
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96
```

```
Asp Leu Tyr Leu Glu Asn Gln Pro Phe Pro Glu Gln
1               5                   10

<210> SEQ ID NO 97
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

His Thr Tyr Lys Tyr Pro Pro Phe Pro Phe Pro Gln
1               5                   10

<210> SEQ ID NO 98
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Glu Gln Pro Phe Pro Glu Val Ile Ile Gly Pro Ala
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Asp Gly Ser Val His Lys Phe Pro Glu Pro Phe Pro
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Phe Pro Gln Leu Glu Gly Cys Thr Phe Phe Pro Glu
1               5                   10

<210> SEQ ID NO 101
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gln Pro Glu Arg Cys Asp Leu Glu Leu Gln Pro Phe
1               5                   10

<210> SEQ ID NO 102
<211> LENGTH: 12
<212> TYPE: PRT
<213> ORGANISM: Artificial Sequence
<220> FEATURE:
```

-continued

<223> OTHER INFORMATION: Description of Artificial Sequence: Synthetic
      peptide

<400> SEQUENCE: 102

Gln Pro Glu Thr Lys Ala Arg Phe Pro Gln Pro Glu
1               5                   10

<210> SEQ ID NO 103
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Phe Pro Gln Arg Asn Glu Phe Gly Glu Phe Pro Glu
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Cys Trp Val Phe Ala Ala Phe Pro Gln Gln Pro Glu
1               5                   10

<210> SEQ ID NO 105
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Phe Pro Glu Leu Ala Glu Lys Glu Glu Gln Pro Glu
1               5                   10

<210> SEQ ID NO 106
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gln Pro Phe Pro Phe Pro Trp Asp Asn Asn Tyr Gly
1               5                   10

<210> SEQ ID NO 107
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Phe Pro Gln Arg Arg Ser Ser Pro Val Phe Pro Glu
1               5                   10

-continued

```
<210> SEQ ID NO 108
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Glu Ser Asn Leu Ile Lys Pro Glu Gln Gln Pro Phe
1               5                   10

<210> SEQ ID NO 109
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Asp Leu Leu Pro Leu His Glu Gln Pro Phe Pro Glu
1               5                   10

<210> SEQ ID NO 110
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Asp Cys Leu Thr Glu Ser Gln Pro Phe Pro Glu Gln
1               5                   10

<210> SEQ ID NO 111
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly His Phe Ile Leu Leu Pro Glu Gln Gln Pro Glu
1               5                   10

<210> SEQ ID NO 112
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Phe Ser Glu Lys Ser Val Phe Pro Glu Gln Pro Glu
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113
```

-continued

```
Gln Pro Glu Glu Gln Pro Thr Val Ser Tyr Asn Gly
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Gly Glu Glu Val Lys Val Pro Glu Gln Pro Glu Gln
1               5                   10

<210> SEQ ID NO 115
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Glu Pro Val Ile Asn Ser Gln Pro Glu Pro Glu Gln
1               5                   10

<210> SEQ ID NO 116
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Glu Glu Glu Arg Gln Glu Glu Gln Pro Gln Pro Phe
1               5                   10

<210> SEQ ID NO 117
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

His His Thr Ala Asp Leu Gln Pro Glu Gln Pro Glu
1               5                   10

<210> SEQ ID NO 118
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gly Thr Lys Tyr Leu Leu Pro Phe Pro Phe Pro Glu
1               5                   10

<210> SEQ ID NO 119
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 119

Glu Gln Pro Thr Phe Thr Val Glu Gly Pro Phe Pro
1               5                   10

<210> SEQ ID NO 120
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gly Glu Ile Gln Gly Asp Gln Pro Glu Gln Pro Phe
1               5                   10

<210> SEQ ID NO 121
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Pro Phe Pro Leu Pro Val Ala Leu Glu Phe Pro Glu
1               5                   10

<210> SEQ ID NO 122
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Cys Ile Leu Tyr Glu Lys Glu Gln Pro Phe Pro Glu
1               5                   10

<210> SEQ ID NO 123
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gln Pro Phe Pro Lys Phe Leu Lys Asn Gln Pro Glu
1               5                   10

<210> SEQ ID NO 124
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Phe Pro Gln Leu Thr Phe Ser Val Val Pro Glu Gln
1               5                   10
```

-continued

```
<210> SEQ ID NO 125
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Pro Phe Pro Glu Gln Pro Val Val Thr Gly Pro Ala
1               5                   10

<210> SEQ ID NO 126
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Glu Lys Tyr Arg Asp Cys Phe Pro Glu Pro Glu Gln
1               5                   10

<210> SEQ ID NO 127
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Pro Phe Pro Thr Ala Thr Val Val Asp Gln Pro Glu
1               5                   10

<210> SEQ ID NO 128
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Pro Phe Pro Leu Asp Val Asn Pro Lys Gln Pro Phe
1               5                   10

<210> SEQ ID NO 129
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Phe Pro Gln Gln Gly Ser Ala Lys Phe Gln Pro Glu
1               5                   10

<210> SEQ ID NO 130
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 130

Pro Phe Pro Arg Asp Glu Arg Glu Asp Gln Pro Phe
1               5                   10

<210> SEQ ID NO 131
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Glu Gln Pro Glu Gln Pro Val Arg Arg Gly Gln Pro
1               5                   10

<210> SEQ ID NO 132
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Pro Phe Pro Ser Val Pro Leu Cys Ile Gln Pro Glu
1               5                   10

<210> SEQ ID NO 133
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ile Leu Gly Glu Pro Lys Gln Pro Phe Gln Pro Glu
1               5                   10

<210> SEQ ID NO 134
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Phe Pro Gln Pro Phe Pro Val Ser Pro Met Ser Trp
1               5                   10

<210> SEQ ID NO 135
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gln Pro Glu Leu His Lys Leu Val Val Gln Pro Glu
1               5                   10

<210> SEQ ID NO 136
<211> LENGTH: 12
<212> TYPE: PRT
```

<213> ORGANISM: Artificial Sequence
<220> FEATURE:
<223> OTHER INFORMATION: Description of Artificial Sequence: Synthetic
     peptide

<400> SEQUENCE: 136

Gly Phe Ile Tyr Gln Gly Phe Pro Gln Pro Phe Pro
1               5                   10

<210> SEQ ID NO 137
<211> LENGTH: 12
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 137

Glu Gln Pro Glu Gln Pro Ala His Ile Thr Asn Asn
1               5                   10

<210> SEQ ID NO 138
<211> LENGTH: 12
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 138

Glu Glu Tyr Val Cys Arg Phe Pro Glu Pro Phe Pro
1               5                   10

<210> SEQ ID NO 139
<211> LENGTH: 12
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 139

Pro Glu Gln Pro Asp Leu Gln Pro Gly Gln Pro Glu
1               5                   10

<210> SEQ ID NO 140
<211> LENGTH: 12
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 140

Gln Pro Phe Phe Pro Gln Thr Thr Pro Ala Asn Ala
1               5                   10

<210> SEQ ID NO 141
<211> LENGTH: 12
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 141

Glu Gln Pro Leu Thr Glu Glu Gln Lys Gln Pro Glu
1               5                   10

```
<210> SEQ ID NO 142
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Glu Ser Asp Lys Leu Lys Gln Pro Phe Pro Glu Gln
1               5                   10

<210> SEQ ID NO 143
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Glu Gln Pro Asn Gly Ile Leu Gly Pro Glu Gln Pro
1               5                   10

<210> SEQ ID NO 144
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Pro Phe Pro Gln Glu Ala Gly Thr Lys Phe Pro Gln
1               5                   10

<210> SEQ ID NO 145
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Glu Glu Thr Gly Met Ala Pro Phe Pro Glu Gln Pro
1               5                   10

<210> SEQ ID NO 146
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Pro Phe Pro Met Ala Met Arg Ile Arg Gln Pro Phe
1               5                   10

<210> SEQ ID NO 147
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 147

Gln Pro Glu Leu Leu Gly Arg Trp Asp Gln Pro Glu
1               5                   10

<210> SEQ ID NO 148
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Asp Ala Pro Phe Val Phe Gln Pro Phe Gln Pro Phe
1               5                   10

<210> SEQ ID NO 149
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ile Glu Tyr Phe Arg Asn Glu Gln Pro Phe Pro Glu
1               5                   10

<210> SEQ ID NO 150
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Gln Pro Glu Ser Thr Lys Tyr Asp Ala Gln Pro Phe
1               5                   10

<210> SEQ ID NO 151
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Cys Leu Ile Leu Leu Asp Gln Pro Glu Pro Phe Pro
1               5                   10

<210> SEQ ID NO 152
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Phe Pro Glu Arg Cys Leu Gly Ile Pro Glu Gln Pro
1               5                   10

<210> SEQ ID NO 153
<211> LENGTH: 12

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Glu Gln Pro Asn Ile Pro Trp Asn Phe Pro Phe Pro
1               5                   10

<210> SEQ ID NO 154
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Gly Asp Lys Ser Glu Met Pro Glu Gln Phe Pro Glu
1               5                   10

<210> SEQ ID NO 155
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Pro Phe Pro Phe Pro Gln Tyr Leu Asp Ser Glu Glu
1               5                   10

<210> SEQ ID NO 156
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Phe Pro Glu Asn Ser Tyr Leu Leu Ala Pro Glu Gln
1               5                   10

<210> SEQ ID NO 157
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Glu Gln Pro Arg Ala Ile Lys Glu Gly Gln Pro Phe
1               5                   10

<210> SEQ ID NO 158
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Cys Thr Val Leu Arg Cys Phe Pro Gln Glu Gln Pro
```

```
1               5                    10

<210> SEQ ID NO 159
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Pro Glu Gln Lys Tyr Gly Gln Cys Trp Phe Pro Gln
1               5                    10

<210> SEQ ID NO 160
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Glu Gly Asp Trp Thr Ala Pro Glu Gln Glu Gln Pro
1               5                    10

<210> SEQ ID NO 161
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Pro Glu Gln Gln Pro Phe Ala Asp Ala Val Tyr Leu
1               5                    10

<210> SEQ ID NO 162
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Pro Phe Pro Leu Lys Ala Val Lys Gly Glu Gln Pro
1               5                    10

<210> SEQ ID NO 163
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Glu Gln Pro Ser Ser Glu Glu Arg Glu Pro Phe Pro
1               5                    10

<210> SEQ ID NO 164
<211> LENGTH: 12
<212> TYPE: PRT
<213> ORGANISM: Artificial Sequence
<220> FEATURE:
<223> OTHER INFORMATION: Description of Artificial Sequence: Synthetic
```

-continued

```
peptide

<400> SEQUENCE: 164

Glu Gln Pro Arg Asp Cys Ser Arg Arg Pro Glu Gln
1               5                   10

<210> SEQ ID NO 165
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Glu Gln Pro Asn Val Ile Ile Gly Pro Phe Pro Glu
1               5                   10

<210> SEQ ID NO 166
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Pro Glu Gln Leu Leu Asn Leu Asn Leu Pro Glu Gln
1               5                   10

<210> SEQ ID NO 167
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Glu Gln Pro Ser Leu Gln Leu Thr Thr Phe Pro Glu
1               5                   10

<210> SEQ ID NO 168
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Pro Glu Gln Asn Leu Glu Pro Phe Ser Gln Pro Phe
1               5                   10

<210> SEQ ID NO 169
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

His Lys Ser Ile Asn Arg Phe Pro Glu Glu Gln Pro
1               5                   10

<210> SEQ ID NO 170
```

-continued

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Glu Gln Pro Leu Arg Arg Trp Lys Asn Pro Glu Gln
1               5                   10

<210> SEQ ID NO 171
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Pro Phe Pro Lys Asn Ala Gly Arg Asp Glu Gln Pro
1               5                   10

<210> SEQ ID NO 172
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Glu Leu Glu Thr Asn Gly Pro Phe Pro Gln Pro Phe
1               5                   10

<210> SEQ ID NO 173
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Tyr Gly Asp Gly Val Ser Gln Pro Glu Gln Pro Phe
1               5                   10

<210> SEQ ID NO 174
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Tyr Gly Asp Gly Val Ser
1               5

<210> SEQ ID NO 175
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175
```

Pro Glu Gln Pro
1

<210> SEQ ID NO 176
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Met Lys Thr Phe Leu Ile Leu Val Leu Leu Ala Thr
1               5                   10

<210> SEQ ID NO 177
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Thr Phe Leu Ile Leu Val Leu Leu Ala Thr Ile Val
1               5                   10

<210> SEQ ID NO 178
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Leu Ile Leu Val Leu Leu Ala Thr Ile Val Ala Thr
1               5                   10

<210> SEQ ID NO 179
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Leu Val Leu Leu Ala Thr Ile Val Ala Thr Ala Thr
1               5                   10

<210> SEQ ID NO 180
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Leu Leu Ala Thr Ile Val Ala Thr Ala Thr Thr Ala
1               5                   10

<210> SEQ ID NO 181
<211> LENGTH: 12
<212> TYPE: PRT
<213> ORGANISM: Artificial Sequence
<220> FEATURE:

-continued

<223> OTHER INFORMATION: Description of Artificial Sequence: Synthetic
      peptide

<400> SEQUENCE: 181

Ala Thr Ile Val Ala Thr Ala Thr Thr Ala Val Arg
1               5                   10

<210> SEQ ID NO 182
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Ile Val Ala Thr Ala Thr Thr Ala Val Arg Phe Pro
1               5                   10

<210> SEQ ID NO 183
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Ala Thr Ala Thr Thr Ala Val Arg Phe Pro Val Pro
1               5                   10

<210> SEQ ID NO 184
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Ala Thr Thr Ala Val Arg Phe Pro Val Pro Gln Leu
1               5                   10

<210> SEQ ID NO 185
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Thr Ala Val Arg Phe Pro Val Pro Gln Leu Gln Pro
1               5                   10

<210> SEQ ID NO 186
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Val Arg Phe Pro Val Pro Gln Leu Gln Pro Gln Asn
1               5                   10

-continued

```
<210> SEQ ID NO 187
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Cys Thr Ile Ala Pro Phe Gly Ile Phe Gly Thr Asn
1               5                   10

<210> SEQ ID NO 188
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Ala Thr Thr Ala Val Arg Phe Pro Val Pro Glu Leu
1               5                   10

<210> SEQ ID NO 189
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Thr Ala Val Arg Phe Pro Val Pro Glu Leu Gln Pro
1               5                   10

<210> SEQ ID NO 190
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Thr Ala Val Arg Phe Pro Val Pro Gln Leu Glu Pro
1               5                   10

<210> SEQ ID NO 191
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Thr Ala Val Arg Phe Pro Val Pro Glu Leu Glu Pro
1               5                   10

<210> SEQ ID NO 192
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192
```

-continued

```
Tyr Gly Asp Gly Val Ser Pro Glu Gln Pro Phe Pro
1               5                   10

<210> SEQ ID NO 193
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Pro Glu Gln Tyr Gly Asp Gly Val Ser Pro Glu Pro
1               5                   10

<210> SEQ ID NO 194
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Pro Glu Gln Pro Glu Pro Tyr Gly Asp Gly Val Ser
1               5                   10
```